(12) United States Patent
Buracas

(10) Patent No.: US 8,248,069 B2
(45) Date of Patent: Aug. 21, 2012

(54) DETECTING SPIN PERTURBATIONS USING MAGNETIC RESONANCE IMAGING

(75) Inventor: Giedrius Buracas, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 416 days.

(21) Appl. No.: 12/555,708

(22) Filed: Sep. 8, 2009

(65) Prior Publication Data
US 2009/0322331 A1    Dec. 31, 2009

Related U.S. Application Data

(63) Continuation-in-part of application No. PCT/US2008/056104, filed on Mar. 6, 2008.

(60) Provisional application No. 60/893,315, filed on Mar. 6, 2007.

(51) Int. Cl.
*G01V 3/00* (2006.01)

(52) U.S. Cl. ....................................................... 324/307

(58) Field of Classification Search ........... 324/300–322
See application file for complete search history.

(56) References Cited

U.S. PATENT DOCUMENTS

| | | | | |
|---|---|---|---|---|
| 5,023,551 | A * | 6/1991 | Kleinberg et al. | 324/303 |
| 6,452,387 | B1 * | 9/2002 | Hargreaves et al. | 324/300 |
| 6,462,545 | B1 | 10/2002 | Busse et al. | |
| 6,714,807 | B2 | 3/2004 | Zur | |
| 6,750,651 | B2 | 6/2004 | Overall | |
| 2005/0033154 | A1 | 2/2005 | DeCharms | |

FOREIGN PATENT DOCUMENTS
EP    0 414 318    2/1991

OTHER PUBLICATIONS

International Search Report and Written Opinion from App. Ser. No. PCT/US2008/056104, dated Aug. 13, 2008, 10 pages.
International Preliminary Report on Patentability for App. Ser. No. PCT/US2008/056104, dated Sep. 8, 2009, 6 pages.
Angelovski et al., "Smart magnetic resonance imaging agents that sense extracellular calcium fluctuations," *Chembiochem.*, 9(11):1729-1734 (2008).
Bangerter, "Analysis of multiple-acquisition SSFP," *Magn. Reson. Med.*, 51:1038-1047 (2004).

(Continued)

*Primary Examiner* — Dixomara Vargas
(74) *Attorney, Agent, or Firm* — Perkins Coie LLP

(57) ABSTRACT

Implementations and examples of systems, apparatus and techniques for using magnetic resonance imaging to measure spin perturbations. In one implementation, a sample containing nuclear spins is magnetized using a principle magnetic field generated external to the sample. A periodic pulse sequence is applied to the sample. The pulse sequence includes multiple radio frequency (rf) pulses and multiple recovery times between the rf pulses. The pulse sequence is configured to generate, in the presence of a magnetic field perturbation, a sequence of multiple different steady states of magnetization in the sample during each period of the pulse sequence. A magnetic resonance signal acquired from the sample is processed to identify characteristics of a magnetic field perturbation in the sample. In some implementations, processing the signal to identify characteristics of a magnetic field perturbation in the sample includes processing the signal to identify characteristics of an electric current in the sample.

38 Claims, 20 Drawing Sheets

OTHER PUBLICATIONS

Biancardi et al., "Combination of BOLD-fMRI and VEP recordings for spin-echo MRI detection of primary magnetic effects caused by neuronal currents," *Magn. Reson. Imaging*, 22:1429-1440 (2004).

Bieri et al., "Balanced alternating steady-state elastography," *Magn. Reson. Med.*, 55:233-241 (2006).

Bodurka, "Toward direct mapping of neuronal activity: MRI detection of ultraweak, transient magnetic field changes," *Magn. Reson. Med.*, 47:1052-58 (2002).

Bodurka et al., "Current-induced magnetic resonance phase imaging," *J. Magn. Reson.*, 137(1):265-271 (1999).

Buracas et al., "Imaging Periodic Currents Using Alternating Balanced Steady-State Free Precession," *Magnetic Resonance in Medicine*, 59:140-148 (2008).

Buracas et al., "Stability of alternating bSSFP signal in the presence of driving perturbations," slides for oral presentation at the International Society for Magnetic Resonance in Medicine Conference, Honolulu, Hawaii, Apr. 2009, 24 pages.

Buracas et al., "Imaging weak currents by means of balanced SSFP," abstract for poster presented at the International Society for Magnetic Resonance in Medicine Conference in Berlin, Germany, May 2007, 1 page.

Buracas et al., "Mapping current waveforms with Multiple Alternating Balanced Steady States," abstract for poster presented at the Human Brain Mapping Conference in Melbourne, Australia, Jun. 2008, 2 pages.

Buracas et al., "Stability of alternating bSSFP signal in the presence of driving perturbations," abstract submitted in Nov. 2008 for presentation at the International Society for Magnetic Resonance in Medicine Conference in Honolulu, Hawaii, Apr. 2009, 1 page.

Cassara et al., "Realistic simulations of neuronal activity: a contribution to the debate on direct detection of neuronal currents by MRI," *Neuroimage*, 39(1):87-106 (2008).

Chu et al., "Hunting for neuronal currents: absence of rapid MRI signal changes during visual-evoked response," *NeuroImage*, 23:1059-67 (2004).

Chow et al., "Investigating direct detection of axon firing in the adult human optic nerve using MRI," *Neuroimage*, 30:835-846 (2006).

Chow et al., "Investigation of MR signal modulation due to magnetic fields from neuronal currents in the adult human optic nerve and visual cortex," *Magn. Reson. Imaging*, 24:681-691 (2006).

Chow et al., "Comparison of BOLD and direct-MR neuronal detection (DND) in the human visual cortex at 3T," *Magn. Reson. Med.*, 60(5):1147-1154 (2008).

Cukur et al., "Multiple repetition time balanced steady-state free precession imaging," *Magn. Reson. Med.*, 62:193-204 (2009).

Dhingra et al., "Synthesis and characterization of a smart contrast agent sensitive to calcium," *Chem. Comm. (Camb)*, (29):3444-3446 (2008).

Dhingra et al., "Towards extracellular Ca2+ sensing by MRI: synthesis and calcium-dependent 1H and 17O relaxation studies of two novel bismacrocyclic Gd3+ complexes," *J. Biol. Inorg. Chem.*, 13(1):35-46 (2008).

Dubois et al., "Frequency-shift based detection of BMS contrast agents using SSFP: potential for MRA," *Magn. Reson. Imaging*, 23(3):453-462 (2005).

Egelman et al., "Calcium dynamics in the extracellular space of mammalian neural tissue," *Biophys. J.*, 76(4):1856-1867 (1999).

Foxall, "Starter sequence for steady-state free precession imaging," *Magn. Reson. Med.*, 53:919-29 (2005).

Freeman et al., "Phase and intensity anomalies in Fourier transform NMR," *J. Magn. Reson.*, 4:366-383 (1971).

Glover, "Simple analytic spiral K-space algorithm," *Magn. Reson. Med.*, 42(2):412-415 (1999).

Gudbjartsson et al., "Simultaneous calculation of flow and diffusion sensitivity in steady-state free precession imaging," *Magn. Reson. Med.*, 34:567-579 (1995).

Hagberg et al., "Challenges for detection of neuronal currents by MRI," *Magn. Reson. Imaging*, 24:483-93 (2006).

Hargreaves et al., "Characterization and reduction of the transient response in steady-state MR imaging," *Magn. Reson. Med.*, 46(1):149-58 (2001).

Hargreaves et al., "Fat-suppressed steady-state free precession imaging using phase detection," *Magn. Reson. Med.*, 50:210-13 (2003).

Hatada et al., "Detection of weak magnetic fields induced by electrical currents with MRI: theoretical and practical limits of sensitivity," *Magn. Reson. Med. Sci.*, 3:159-163 (2004).

Kamei et al., "Neuronal current distribution imaging using magnetic resonance," *IEEE Trans. Magn.*, 35:4109-4111 (1999).

Konn et al., "MRI detection of weak magnetic fields due to an extended current dipole in a conducting sphere: a model for direct detection of neuronal currents in the brain," *Magn. Reson. Med.*, 50:40-49 (2003).

Konn et al., "Initial attempts at directly detecting alpha wave activity in the brain using MRI," *Magn. Reson. Imaging*, 22:1413-1427 (2004).

Lee et al., "Respiration-induced B0 field fluctuation compensation in balanced SSFP: real-time approach for transition-band SSFP fMRI," *Magn. Reson. Med.*, 55:1197-1201 (2006).

Lee et al., "Complex data analysis in high-resolution SSFP fMRI," *Magn. Reson. Med.*, 57:905-917 (2007).

Liston et al., "The MR detection of neuronal depolarization during 3-Hz spike-and-wave complexes in generalized epilepsy," *Magn. Reson. Imaging*, 22:1441-1444 (2004).

Mandelkow et al., "Heart beats brain: The problem of detecting alpha waves by neuronal current imaging in joint EEG-MRI experiments," *NeuroImage*, 37:149-163 (2007).

Miller et al., "Functional brain imaging using a blood oxygenation sensitive steady state," *Magn. Reson. Med.*, 50:675-83 (2003).

Mishra et al., "Facile synthesis and relaxation properties of novel bispolyazamacrocyclic Gd3+ complexes: an attempt towards calcium-sensitive MRI contrast agents," *Inorg. Chem.*, 47(4):1370-1381 (2008).

Nayak, "Spiral balanced steady-state free precession cardiac imaging," *Magn. Reson. Med.*, 53:1468-73 (2005).

Nicholson et al., "Potassium, calcium, chloride and sodium changes in extracellular space during spreading depression in cerebellum," *Arzneimittelforschung*, 28(5):874-875 (1978).

Ogawa et al., "Brain magnetic resonance imaging with contrast dependent on blood oxygenation," *Proc. Natl. Acad. Sci U.S.A.*, 87(24):9868-72 (1990).

Overall et al., "Oscillating dual-equilibrium steady-state angiography," *Magn. Reson. Med.*, 47:513-522 (2002).

Petridou et al., "Direct magnetic resonance detection of neuronal electrical activity," *PNAS*, 103:16015-16020 (2006).

Scheffler et al., "Oscillating steady states," *Magn. Reson. Med.*, 55:598-603 (2006).

Scheffler et al., "Is TrueFISP a gradient-echo or a spin-echo sequence?," *Magn. Reson. Med.*, 49:395-7 (2003).

Scheffler et al., "On the transient phase of balanced SSFP sequences," *Magn. Reson. Med.*, 49:781-3 (2003).

Scheffler et al., "Principles and applications of balanced SSFP techniques," *Eur. Radiol.*, 13:2409-18 (2003).

Scheffler, "A pictorial description of steady-states in rapid magnetic resonance imaging," *Concepts in Magn. Reson.*, 11:291-304 (1999).

Schneiders, "Solutions of two paramagnetic ions for use in nuclear magnetic resonance phantoms," *Med. Phys.*, 15(1):12-16 (1988).

Vasanawala et al., "Fluctuating equilibrium MRI," *Magn. Reson. Med.*, 42(5):876-883 (1999).

Xiong et al., "Directly mapping magnetic field effects of neuronal activity by magnetic resonance imaging," *Hum. Brain Mapp.*, 20:41-9 (2003).

Xue et al., "Direct MRI mapping of neuronal activity evoked by electrical stimulation of the median nerve at the right wrist," *Magn. Reson. Med.*, 61(5):1073-1082 (2009).

Wansapura et al., "NMR relaxation times in the human brain at 3.0 tesla," *Magn. Reson. Imaging*, 9:531-538 (1999).

Yang et al., "Mapping of periodic waveforms using the ghost reconstructed alternating current estimation (GRACE) magnetic resonance imaging technique," *Magn. Reson. Med.*, 50:633-637 (2003).

Zhao et al., "B(0)-fluctuation-induced temporal variation in EPI image series due to the disturbance of steady-state free precession," *Magn. Reson. Med.*, 44:758-65 (2000).

Zur et al., "An analysis of fast imaging sequences with steady-state transverse magnetization refocusing," *Magn. Reson. Med.*, 6:175-193 (1988).

Egelman, et al., "Computational Properties of Peri-Dendritic Calcium Fluctuations," The Journal of Neuroscience, 18(21):8580-8589, Nov. 1998.

* cited by examiner

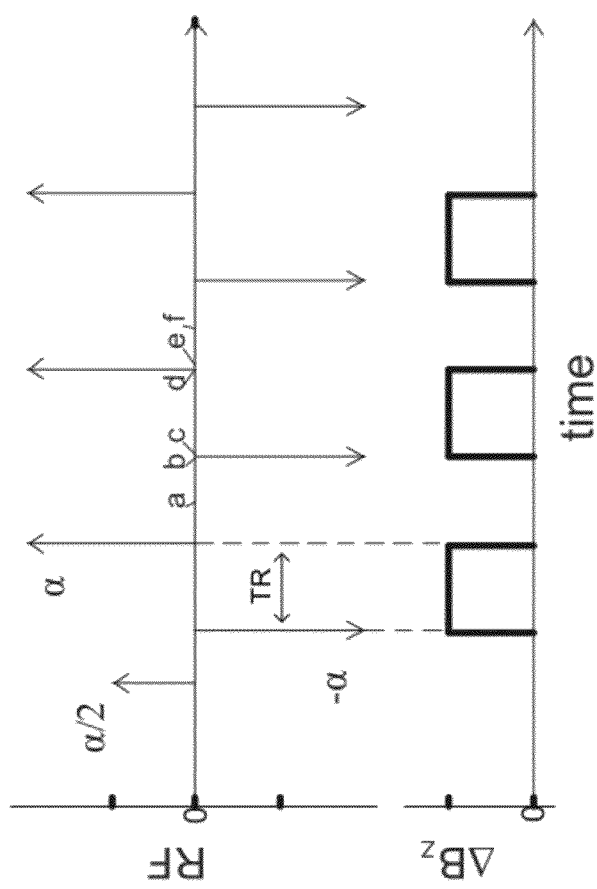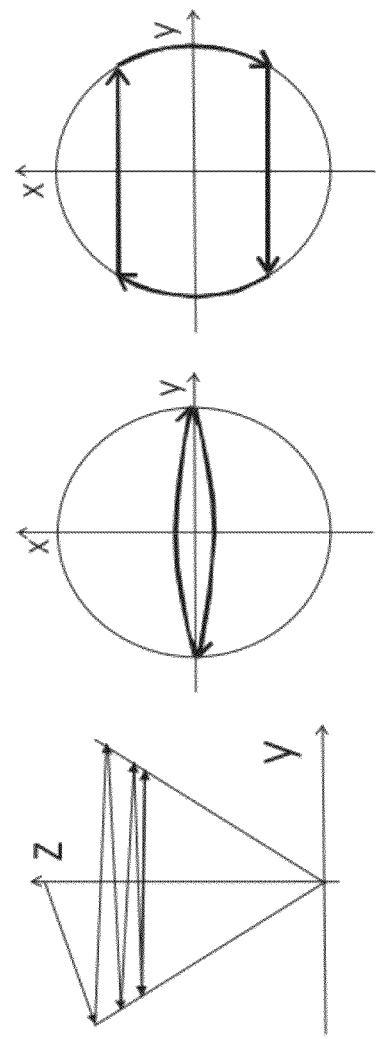

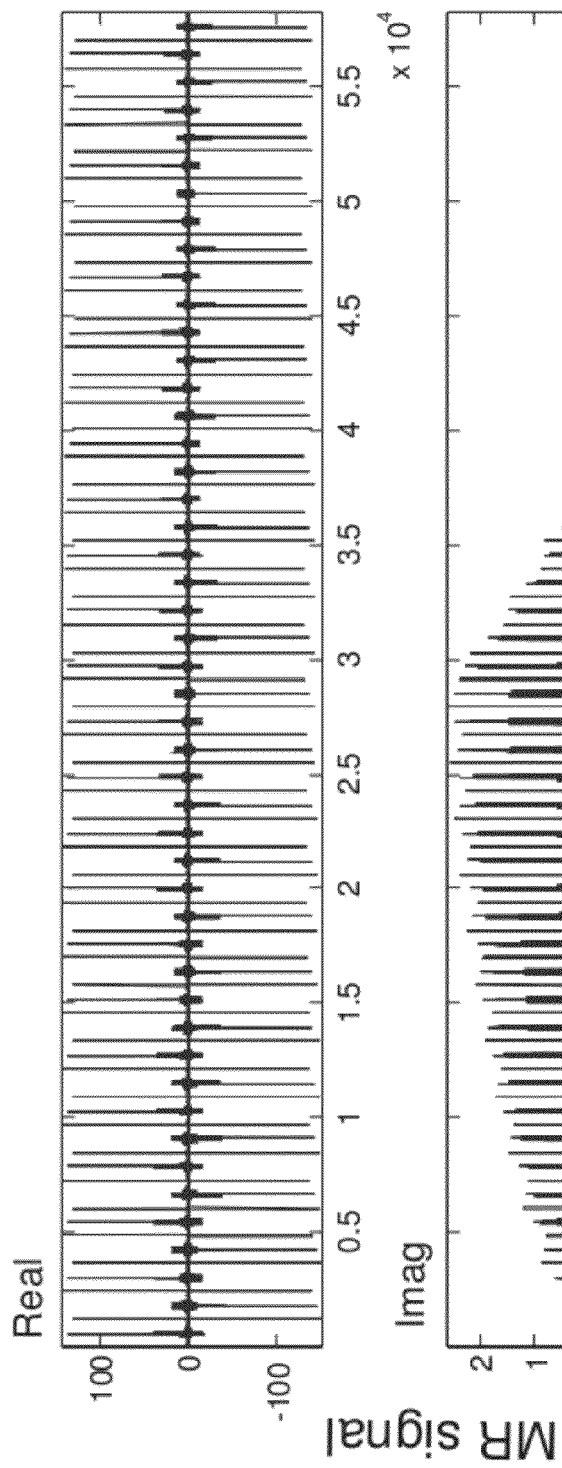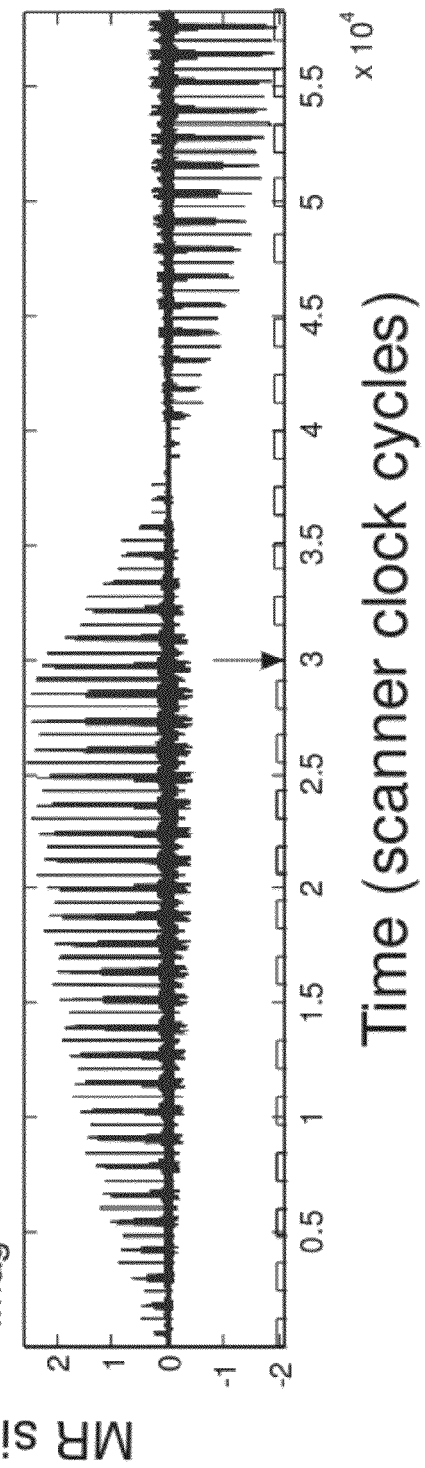
FIG. 5A
FIG. 5B

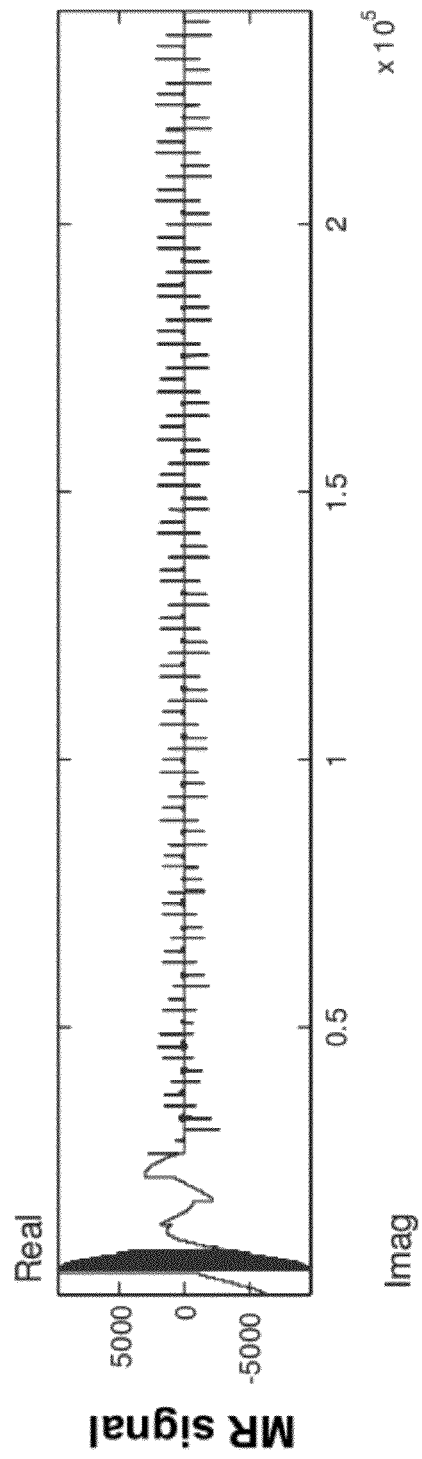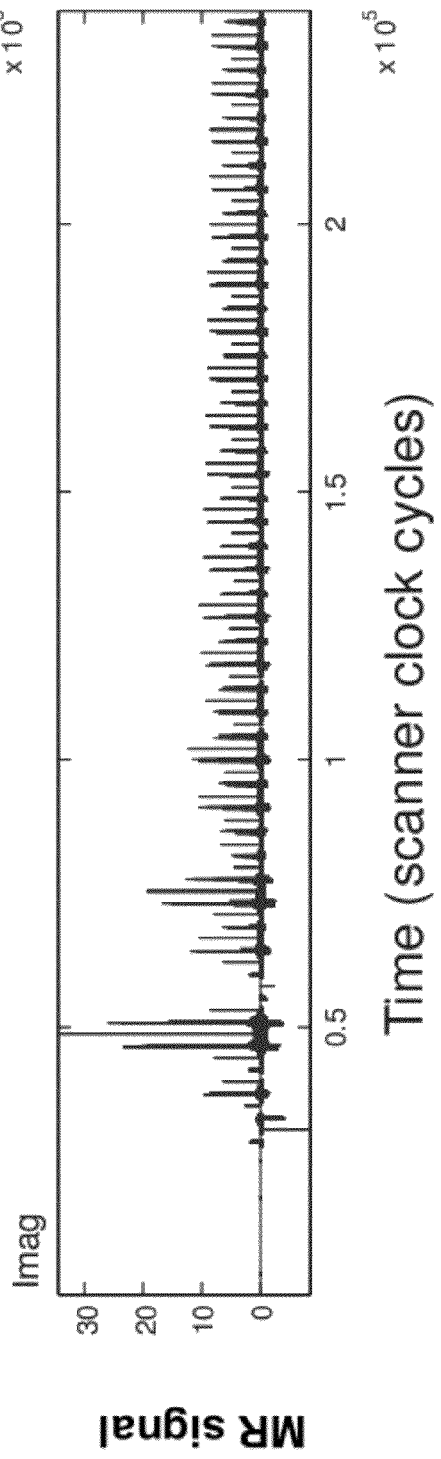

Image magnitude of Δcomplex

Δ magnitude

Δ phase

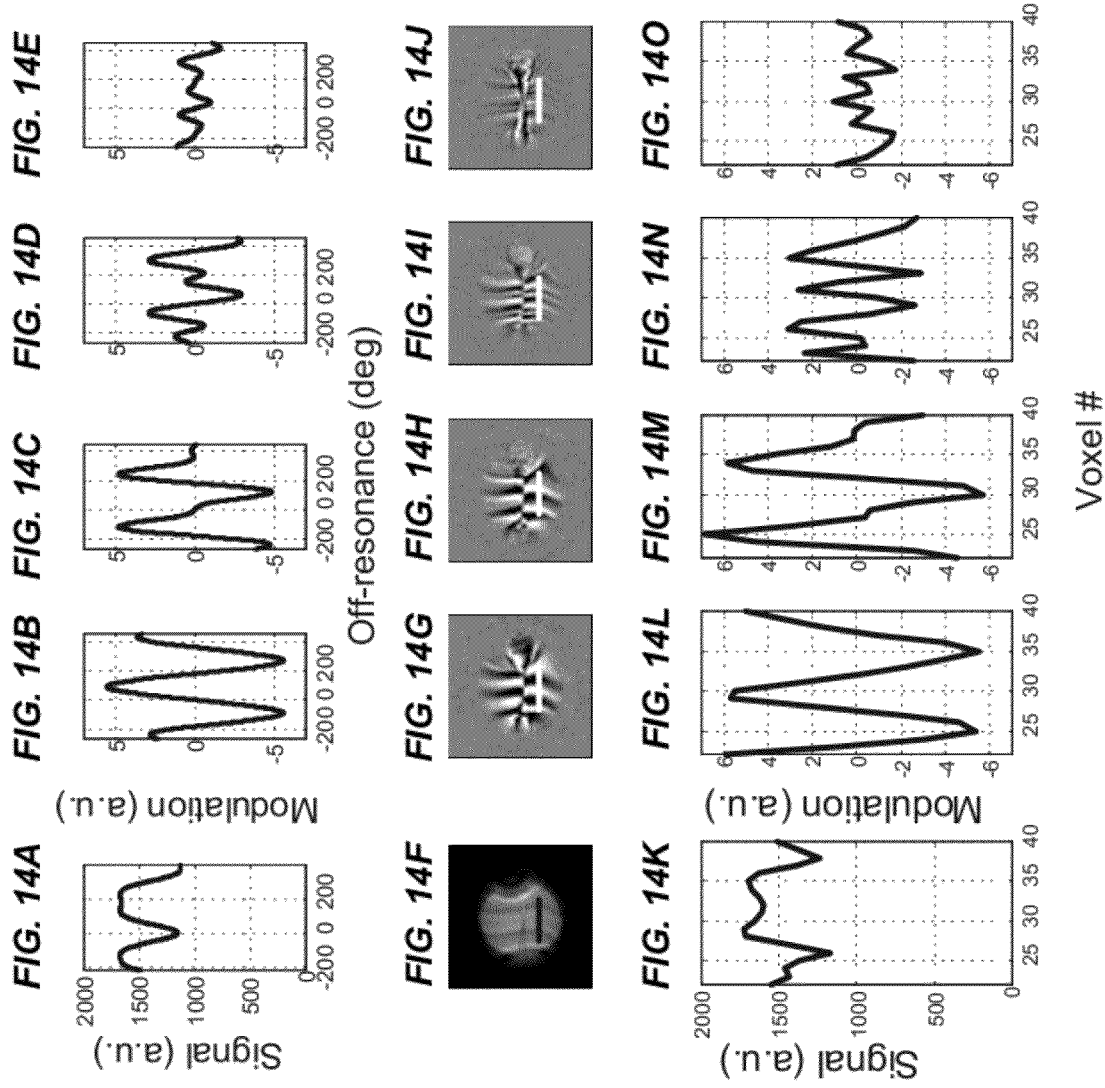

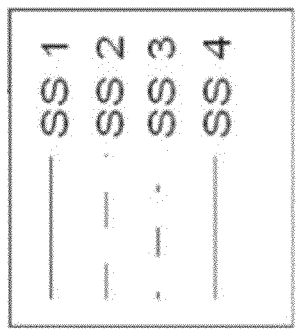
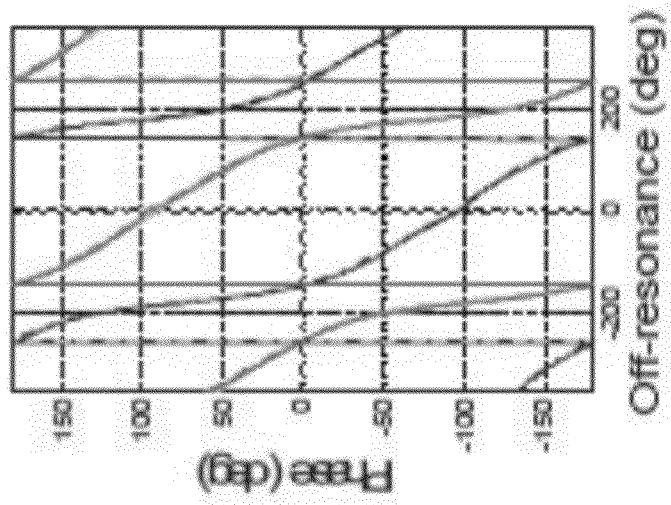
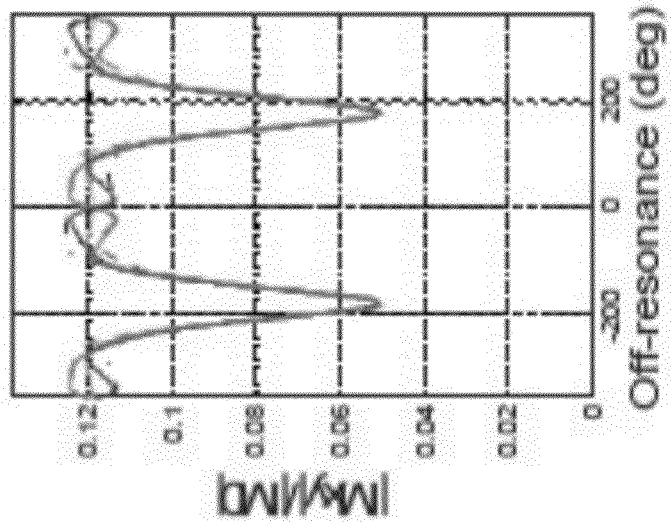

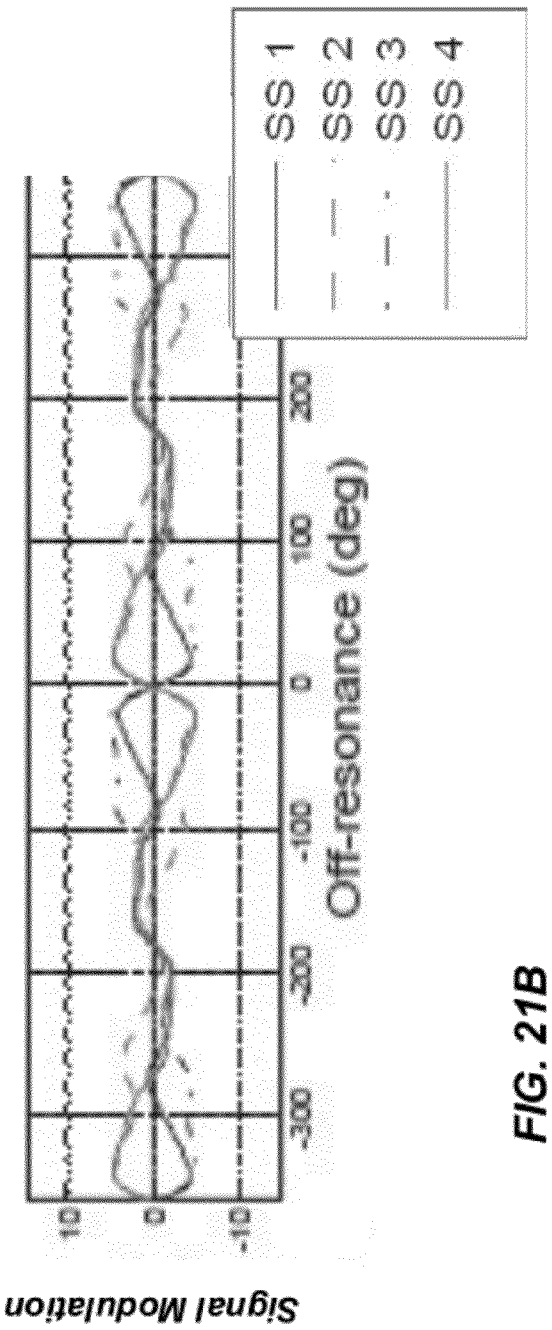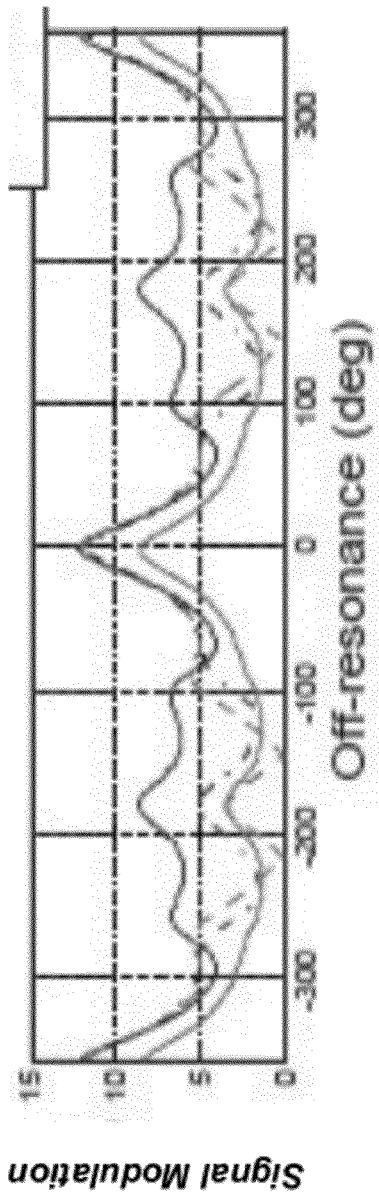
FIG. 21A
FIG. 21B

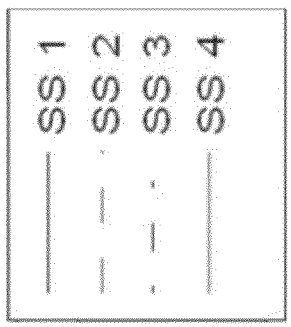
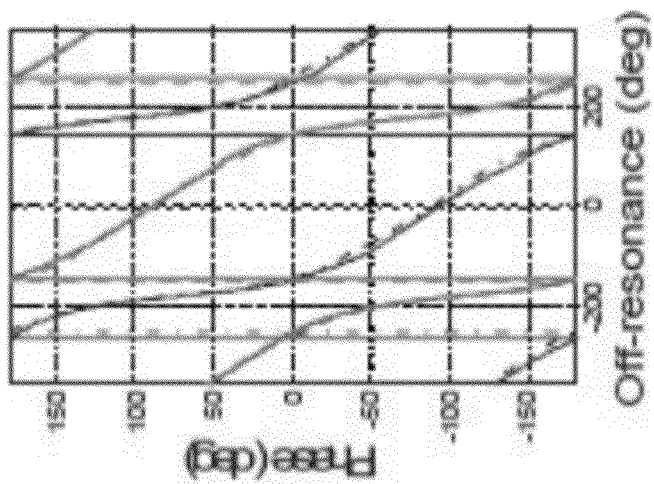
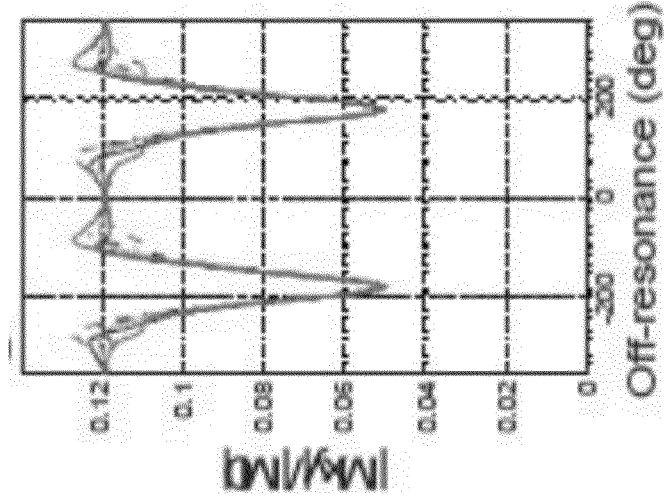
FIG. 22B
FIG. 22A

DETECTING SPIN PERTURBATIONS USING MAGNETIC RESONANCE IMAGING

CROSS-REFERENCE TO RELATED APPLICATIONS

This application is a continuation-in-part of international application PCT/US2008/056104 entitled "Detecting Spin Perturbations Using Magnetic Resonance Imaging" and filed on Mar. 6, 2008, which is related to and claims the benefit of U.S. provisional application Ser. No. 60/893,315 entitled "Measuring Weak Periodic and Quasi-Periodic Magnetic Fields Using Magnetic Resonance Imaging (MRI)" and filed Mar. 6, 2007, both of which are incorporated herein by reference.

BACKGROUND

The present disclosure relates to magnetic resonance imaging (MRI).

MRI techniques have been widely applied in imaging applications in medical, biological and other fields. A typical MRI technique uses radio frequency (rf) magnetic field pulses to manipulate the magnetic spins in a subject and processes measured responses from the magnetic spins to produce an image of the subject or a portion of the subject. An MRI system may include hardware to generate various magnetic fields for imaging, including a static magnetic field ($B_0$) along a z-direction to polarize a portion of the magnetic spins, gradient fields along mutually orthogonal x, y, or z directions, and an rf magnetic field to manipulate the spins. Functional MRI techniques measure variations in the blood flow in the brain to indicate the distribution of the brain activities.

SUMMARY

This application includes implementations and examples of systems, apparatus and techniques for using magnetic resonance imaging to measure spin perturbations. In one aspect, a sample containing nuclear spins is magnetized using a principle magnetic field generated external to the sample. A periodic pulse sequence is applied to the sample. The pulse sequence includes multiple radio frequency (rf) pulses and multiple recovery times between the rf pulses. The pulse sequence is configured to generate, in the presence of a magnetic field perturbation, a sequence of multiple different steady states of magnetization in the sample during each period of the pulse sequence. A magnetic resonance signal acquired from the sample is processed to identify characteristics of a magnetic field perturbation in the sample. In some implementations, processing the signal to identify characteristics of a magnetic field perturbation in the sample includes processing the signal to identify characteristics of an electric current in the sample.

In one or more embodiments, rf pulses are applied in synchronization with time-dependent perturbations to the principal magnetic field in order to measure a magnetic resonance signal in a steady state to obtain a long phase integration time. In such an implementation, the measured magnetic resonance signal is processed to uncover a weak periodic or quasi-periodic signal carried by the measured magnetic resonance signal.

In one or more embodiments, a magnetic resonance imaging (MRI) system is used to implement rf pulse sequences and data processing. The MRI system includes an rf component for applying rf pulses and a data processing component for processing magnetic resonance signals.

The characteristics of the magnetic field perturbation can include a location of the magnetic field perturbation, a spatial distribution of the magnetic field perturbation, an amplitude of the magnetic field perturbation, or a time-dependent waveform of the magnetic field perturbation. Embodiments may also include one or more of the following features. Processing a magnetic resonance signal acquired from the sample to identify characteristics of a magnetic field perturbation in the sample can include processing a magnetic resonance signal acquired from the sample to identify a phase applied to the magnetization by the magnetic field perturbation during each period of the pulse sequence. The time duration of each period of the pulse sequence can be based at least in part on a period of a magnetic field perturbation in the sample.

Processing a magnetic resonance signal acquired from the sample to identify characteristics of a magnetic field perturbation in the sample can include processing a magnetic resonance signal acquired from the sample to identify characteristics of an electric current in the sample.

The sample can include at least part of a nervous system. The sample can include at least part of a central nervous system or at least part of a peripheral nervous system. Processing a magnetic resonance signal acquired from the sample to identify characteristics of a magnetic field perturbation in the sample can include processing a magnetic resonance signal acquired from the sample to identify characteristics of a neuronal current in the nervous system. The nervous system may include a contrast agent that tracks correlates of neuronal activity. The contrast agent can include a smart contrast agent having at least one of a T2 relaxation rate or bulk susceptibility that changes as a function of Ca++ concentration in the nervous system. For example, the MABSS technique is suitable, in some instances, for detection and waveform measurement at a fine temporal scale (e.g., time scales of 10-100 ms, or another time scale) of neuronal activity correlates (such as, for example, extra-cellular Ca++), and the neuronal activity correlates can be amplified by means of smart contrast agents exhibiting T2 relaxivity or bulk magnetic susceptability changes as a function of Ca++ concentration.

The sample can include a blood vessel. Processing a magnetic resonance signal acquired from the sample to identify characteristics of a magnetic field perturbation in the sample can include processing a magnetic resonance signal acquired from the sample to identify characteristics of a fluid flow in the blood vessel. In other cases, processing a magnetic resonance signal acquired from the sample to identify characteristics of a magnetic field perturbation in the sample can include processing a magnetic resonance signal acquired from the sample to identify characteristics of mechanical perturbations applied to the sample.

A motion sensitizing gradient can be applied to the sample. Applying a motion sensitizing gradient to the sample can include controlling the motion sensitizing gradient to measure characteristics of diffusion in the sample.

The magnetic field perturbation in the sample can be induced. Inducing the magnetic field perturbation in the sample can include mechanically perturbing the sample. Inducing the magnetic field perturbation in the sample can include inducing the magnetic field perturbation in the sample in a periodic manner, and the time duration of each period of the pulse sequence can be based at least in part on a period of the induced magnetic field perturbation. The sample can include at least a portion of a living organism, and inducing the magnetic field perturbation can include presenting a sensory stimulus to the living organism.

The details of one or more implementations are set forth in the accompanying drawings and the description below. Other features will be apparent from the description and drawings, and from the claims.

DESCRIPTION OF DRAWINGS

FIG. 1 is a plot illustrating an example pulse sequence and perturbation.

FIGS. 2A-C are plots illustrating example evolution of magnetization during an example pulse sequence.

FIGS. 5A-B are plots illustrating example simulated magnetic resonance signals.

FIG. 6 is a plot illustrating an example simulated magnetic resonance signal.

FIG. 7 is a plot illustrating an example simulated magnetic resonance signal.

FIGS. 14A-E and 14K-O are plots illustrating example simulated magnetic resonance signals. FIGS. 14F-J are example images constructed from magnetic resonance signals.

FIG. 20A is a plot illustrating the amplitude of an example simulated magnetic resonance signal. FIG. 20B is a plot illustrating the amplitude of an example simulated magnetic resonance signal.

FIGS. 21A-B are plots illustrating modulation of an example simulated magnetic resonance signal.

FIG. 22A is a plot illustrating the amplitude of an example simulated magnetic resonance signal. FIG. 22B is a plot illustrating the amplitude of an example simulated magnetic resonance signal.

Like reference symbols in the various drawings indicate like elements.

DETAILED DESCRIPTION

Figure 3A:
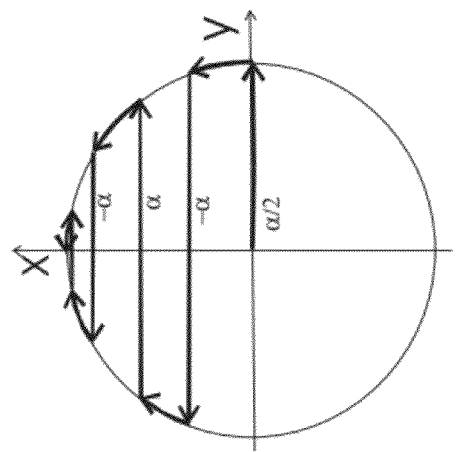
FIGS. 3A-B are plots illustrating an example evolution of magnetization during an example pulse sequence.

This application describes systems, apparatus and techniques for obtaining properties of a sample based on a spatial distribution, amplitude, and/or temporal waveform of a magnetic perturbation using magnetic resonance imaging (MRI). According to some implementations, perturbations in transverse spin phase are integrated over long times. A periodic spin phase perturbation can be effectively amplified by integrating over many periods of the perturbation. Examples of spin phase modulating factors include a periodic offset of the magnetic field along the z axis induced by electric currents, a periodic displacement of spins in a magnetic field gradient due to mechanic oscillations, motion sensitizing gradients used for imaging flow and diffusion, and other factors. A motion sensitizing gradient includes balanced gradients, and may be used to generate balanced steady states. In some implementations, a first pulse sequence technique (e.g., a technique referred to herein as dual alternating balanced steady states—DABSS) can be used to measure the amplitude of a spin phase modulating factor, while a second pulse sequence technique (e.g., a technique referred to herein as multiple alternating balanced steady states—MABSS) can be used to measure the waveform of the spin phase modulating factor. In addition, a robust method for imaging periodic dynamic spin phase perturbations of low amplitude that can be applicable for imaging neuronal activation waveforms by means of neuron current MRI (ncMRI) or smart MRI contrast agents (SCAs) at a short temporal scale (e.g., 10-100 ms in some implementations).

In some implementations, a spatial distribution and amplitude of a weak magnetic field of a known frequency and phase is measured by MRI. Example pulse sequences for such measurements are based on a balanced free precession steady state (bSSFP) pulse sequence (which may also known be as TrueFISP, FIESTA, or balanced FFE). In some examples, a pulse sequence induces an alternating balanced steady state (ABSS), wherein a component of magnetization traverses a periodic cycle of steady states. When the periodic cycle includes only two different steady states, the technique is referred to as dual alternating balanced steady states (DABSS). When the periodic cycle includes more than two different steady states, the technique is referred to as multiple alternating balanced steady states (MABSS). Some processes that utilize a DABSS technique are also referred to as phase-accumulation at steady state (PASS) techniques. In some implementations, ABSS enables efficient temporal integration of variations in spin phase caused by a weak quasi-periodic modulation of the offset of the main magnetic field $\Delta B_z$. Time-varying and spatially localized offsets in spin phase can be induced, for example, by magnetic field variations associated with externally applied electric currents or electric currents generated by neural and muscular tissue spontaneously or evoked in response to patterned stimulation. Some implementations include measuring induced and naturally occurring electrical activity in the brain and other electrogenic organs in humans and animals. Some implementations include measuring electrical currents induced in other types of objects that are also compatible with MRI. Some implementations include measuring quasi-periodic brain activities, both spontaneous activities and activities associated with sensory, motor, and cognitive processes. Some implementations include measuring a temporal waveform of spin phase perturbations associated with spin motion in a magnetic field gradient, including spin motion produced by mechanical waves for the purpose of elastography and motion due to perfusion and diffusion.

For example, a mechanism is described for direct measurement of weak quasi-periodic electrical activity in living tissues and other MRI-compatible objects. Improved temporal resolution and the direct nature of ABSS-based techniques can, in some implementations, yield both fundamental and diagnostic information that is not available using some other techniques. Direct measurement of weak magnetic fields generated by the brain opens a way to bypass responses in vasculature and focus on neuronal activity directly. In some practical applications, this direct measurement mechanism can be implemented to improve the signal to noise ratio of a magnetic resonance signal.

Some example implementations include synchronizing periodic variation of $\Delta B_z$ to the timing of rf excitation pulses in order to measure the MR signal in a steady state free precession (SSFP) regime. In such an implementation, signal phase integration times can be extended by up to an order of magnitude or more, thus affording much higher sensitivity, which typically is directly proportional to the phase integration time.

The pulse sequences and other techniques disclosed herein may be employed in a variety of clinical, biological, and other applications. For example, direct imaging of neuronal currents in the brain using MRI may provide a promising alternative to other brain imaging methods. In some implementations, ABSS-based techniques allow very high spatial resolution MRI-based magnetoencephalography.

In an example implementation, an MR signal perturbation produced by weak (quasi-) periodic magnetic field fluctuations is amplified and measured. Specifically, small electric currents whose vector is oriented perpendicular to the main magnetic field ($B_0$) of an MRI scanner add (or subtract) a small value of $\pm\Delta B_z$ to $B_0$ in the vicinity of the current conductor. Thus measurement of the $\Delta B_z$ may help identify the location of the underlying current dipole. In case $\Delta B_z$ is very small (e.g. cortical current dipoles generate $\Delta B_z$ of order 0.1-1 nanofarad (nF)), it may be advantageous to accumulate the phase produced by $\Delta B_z$ to the supra-threshold value for detection, since SNR is proportional to the phase accumulation time.

Pulse sequences for imaging of phase deviations ($\Delta\phi$) include gradient echo and spin echo with echoplanar acquisition. In a typical implementation, a $\Delta B_z$ pulse is placed immediately after the 90 degree excitation pulse and before the refocusing 180 degree pulse in case of spin echo. The phase accumulation time in these pulse sequences may be constrained by echo time TE (e.g., <100 msec). At high field (e.g., 3 Tesla) $T_2$ and $T_2^*$ decay times are further foreshortened, and thus even shorter TE (e.g., 30 msec) times are typically used.

In some implementations, a phase integration time is substantially extended, which can significantly improve the SNR of the signal produced by small periodic magnetic fields. In such an implementation, a driving sequence or stimulus that drives the magnetic field fluctuations is phase locked to rf pulses of an ABSS-based technique. Synchronization of the rf pulses with the oscillating magnetic field $\Delta B_z$ may result in continuous accumulation of the phase deviations produced by the periodic magnetic pulsation.

FIG. 1 illustrates an example MRI pulse sequence in accordance with some aspects of the present disclosure. The horizontal axes represents time. The top plot represents the initial eight rf pulses of the example pulse sequence. The flip angle $\alpha$ is typically small. For example, $\alpha$ may be in the range of 10 to 50 degrees. In some cases, an optimal value of $\alpha$ can be calculated from the equation $$\cos(\alpha)=(T1/T2-1)/(T1/T2+1).$$

The example pulse sequence starts with a catalytic rf pulse to rotate the magnetization by an angle $\alpha/2$, and the pulse sequence then alternates between rf pulses rotating the magnetization by angles $-\alpha$ and $\alpha$. The bottom trace in FIG. 1 illustrates the time-course of the $B_0$ fluctuation, which is a magnetic field perturbation. The rf pulses are approximately phase locked to zero-crossings in the internally or externally driven magnetic field fluctuation. The example pulse sequence in FIG. 9A is configured to implement dual-state ABSS (DABSS). A full period of RF excitation and current perturbation is played out between time points a and f.

A bSSFP pulse sequence includes gradients that are rewound on all axes (i.e., balanced), short repetition time (e.g., TR less than T1 and/or T2) and relatively low tip angle (e.g., 0 to 90 degrees). In some implementations of a bSSFP pulse sequence, a time integral of gradient fields applied during the pulse sequence is zero. Magnetization can reach a steady state approximately after a time of 5*T1/TR. In some cases, the transient phase includes salient off-resonance-dependent oscillations. These oscillations and the duration of approach to equilibrium can be foreshortened by application of catalytic preparatory sequences with alternating flip angle and phase. In some implementations, at the zero resonance offset, the signal immediately after an excitation pulse is equal to: $bSSFP = M0 \sin(\alpha)e2(1-E1)/[1-(E1-E2)\cos(\alpha)-E1E2]$; where $E1=\exp(-TR/T1)$, $E2=\exp(-TR/T2)$, and $e2=\exp(-TE/T2)$.

FIGS. 2A-C illustrate evolution of magnetization during an example bSSFP pulse sequence. Horizontal lines correspond to a rotation of the magnetization by the rf pulse (around the x axis). In FIG. 2A, an example evolution of the projection of magnetization vector of an isochromat in a voxel to the y-z plane during the transient phase is plotted. In FIG. 2B, an example progression of the transverse magnetization (x-y plane) during steady state in the absence of resonance offsets (i.e., zero dephasing) is plotted. In FIG. 2C, an example progression of the transverse magnetization (x-y plane) during steady state in the presence of resonance offsets (i.e., non-zero dephasing) is plotted.

In some examples, in the presence of static $\Delta B_z$ inhomogeneities, transverse magnetization is subject to dephasing, as in FIG. 2C. The dephasing behavior, however, may be modified when the inhomogeneity oscillates and is phase-locked to alternating rf pulses (e.g., when $\Delta B_z(n)=\Delta B_z(n+2)$, where n is the index of time interval). For the example magnetic field offsets that alternate sign $\Delta B_z(n)=-\Delta B_z(n+1)$ in FIG. 1, the transverse magnetization follows the path as in FIG. 3A. In effect the x-component of the magnetization accrues with time in the example. In the brain, periodic, oscillatory reversals of the current dipole vector (which may be estimated by MEG) occur both spontaneously and in response to various stimuli.

Similar phase accumulation, albeit along a different evolution path, can also occur if the oscillating offset $\Delta B_z(t)$ is alternating between a constant value and zero. The latter pattern of oscillation can be induced by stimulating neuronal activity with periodic stimuli of various modalities. Example modalities include motor and cognitive activity patterned according to a periodic cueing signal, which would also evoke similar brain activation.

Figure 3B:
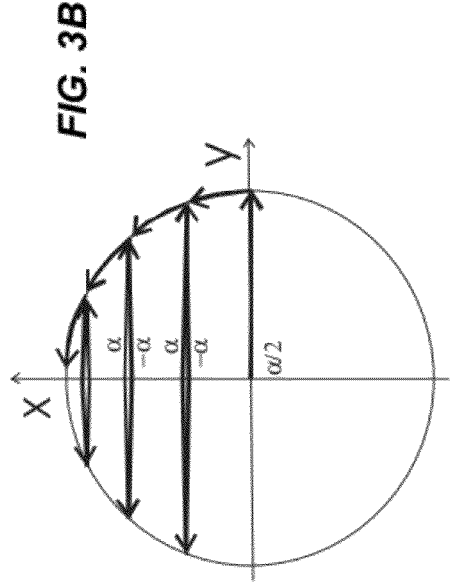

FIGS. 3A-B illustrate an example evolution of transverse magnetization under the influence of the phase-locked oscillating $\Delta B_z(t)$. In FIG. 3A, the plot demonstrates an example effect on the transverse magnetization of an oscillating $\Delta B_z(t)$ that alternates the sign with every TR, as shown in the bottom trace of FIG. 1. In FIG. 3B, the plot demonstrates an example effect of the oscillating offset that alternates between a constant positive value and zero. In both examples, the x component of the transverse magnetization grows as the phase offset is accumulated.

The MR signal generated using the ABSS technique can be spatially encoded for imaging in a variety of MRI techniques. In a bSSFP sequence, imaging gradients (e.g. slice select gradients, phase encode gradients, and frequency encode gradients) are completely rewound before the next rf pulse and the steady state thus is not affected by the choice of imaging gradients. Therefore, any acquisition process that does not violate bSSFP constraints (e.g., short TR less than T1 and T2, balanced gradients) can be inserted between subsequent excitations. Examples include one-shot and interleaved spiral, echoplanar and 3D segmented acquisition. Parallel imaging may shorten acquisition times. TR may affect the spin precession (dephasing) angle θ occurring between excitations. In some implementations, the angle does not exceed 180 degrees so that the signal is refocused at TE=TR/2. Factors such as $B_0$ inhomogeneity and flow effects may be considered when determining an acquisition process.

Figure 4A:
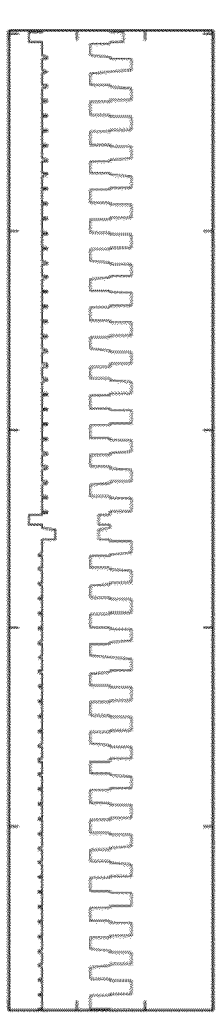
FIG. 4A is a plot illustrating an example gradient sequence.
Figure 4B:
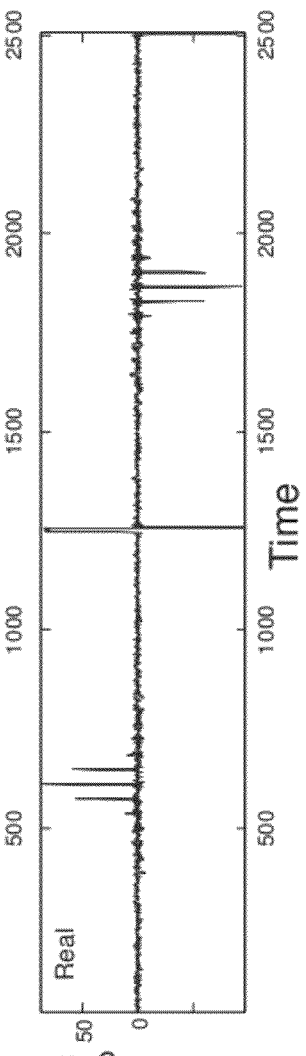
FIG. 4B is a plot illustrating an example an example simulated magnetic resonance signal.

In some of the example computer simulations presented in this disclosure, for example in FIGS. 4A-B, a simple one-shot echoplanar imaging acquisition was used. However, the choice of the acquisition process for these simulations does not affect the generality of conclusions drawn about the ABSS-based techniques used.

FIGS. 4A-B show an example where an echo-planar acquisition is used in conjunction with bSSFP. In FIG. 4A, the phase (top trace) and frequency (bottom trace) encode gradients were balanced to yield zero net area. In FIG. 4B, the plot illustrates the real part of the MR signal generated in the absence of $B_0$ inhomogeneity. The imaginary part is nearly zero.

FIGS. 5A-B illustrate an example MRI signal produced by numerically simulating evolution of a spin system of a virtual phantom. In the example, the initial magnetization is normalized to a value of 1, and relaxation constants T1/T2=1200/60 msec are used. The simulation was implemented by solving the Bloch equations numerically with a 4 microsecond (usec) resolution (i.e., scanner clock cycle) for a time duration of 0.42 sec. In the simulation, a total of 48 excitations were applied. Each excitation corresponded to a flip angle of α=21 degrees and, and the recovery times TR=18 milliseconds (msec). Each excitation was followed by a full EPI readout resulting in a standard EPI echo train, alternating in sign on the real axis due to 180 degree phase cycling. In the example simulation, the field of view (FOV) was 25.6 cm, the image matrix was 64×64 in size, and the signal was acquired over a frequency range of 0±125 KHz.

In the example simulation, the phase offset alternated between 0 and 1 Hz within a localized area at the center of the circle (see, for example, FIGS. 4A-B and FIGS. 6A-D). For the initial 24 TRs the signal alternated as [1,0,1, . . . ]. As a result, the phase of the signal component representing the alternating offset in the center of the phantom drifted into the imaginary part of the signal due to the phase convergence on the x axis (see FIG. 3). The phase of the offset alternation for the remaining 24 TRs was changed to [0,1,0, . . . ]. This change forced magnetization along the x axis to diverge and converge on the x axis with the opposite sign thus resulting in the change in the sign of the imaginary component of the MR signal. Thus, the phase of the spatially encoded MR signal representing imaged area that is undergoing periodic excitation phase-locked variation can be manipulated depending on the phase of the periodic offset variation. This manipulation can be used to produce a unique temporal signature of the signal so that it is distinguishable from structured noise sources (e.g. BOLD activation, periodic physiological noise, and others).

FIGS. 5A and 5B show the MR signal generated by an example ABSS-based imaging technique in the absence of static $B_0$ field offsets. The real and imaginary parts of the MR signal are plotted in FIGS. 5A and 5B, respectively (note the scale difference between the two plots). In the example, the real part of the signal results from the whole phantom, but the imaginary part is dominated by signal originating in the area undergoing periodic offset variations. Bars at the bottom of image graph represent times when the 1 Hz offset was on during the simulation. The signal was acquired over 48 TRs and the phase of the driving stimulus was changed after 24 TRs (as indicated by the arrow in the bottom plot).

In the example simulation, each gradient echo train following an rf pulse encodes an image of the simulated phantom. The contrast of the region with alternating offset grows with each excitation throughout the 24 TR interval until the direction of spin phase accumulation is reversed by the change in the phase of the driving signal. This indicates that the effect of variable $B_0$ offset on the phase ($\Delta \phi$) is accumulated for the duration of 24*TR≈400 msec. Such duration of phase integration is prohibitive in example gradient and spin echo experiments due to T2* and T2 relaxation (respectively).

With regard to the simulated MR signals, the SNR of the signal produced by the alternating offset can be increased by $\sqrt{2}$ if the MR signals of two consecutive TR intervals are averaged together in complex domain. This effectively cancels the signal due to the zero offset region (e.g., FIG. 5A) and doubles the signal generated by the region with alternating offset.

In some implementations, in the presence of off-resonance static offsets, the transmit frequency is selected at the median of the frequency distribution of off-resonance isochromats and a catalytic preparatory sequence is applied before starting the balanced SSFP sequence in order to suppress extensive transient oscillations. Under these conditions the magnetization of the spin system whose offset $\Delta B_z$ is driven periodically may converge along the x axis as in the absence of static offsets (see, for example, FIGS. 6 and 7). When manipulating the accumulation of the spin phase with the driving stimulus, some residual oscillations may confound the measured MR signal.

FIGS. 6 and 7 show the MR signal generated by an example imaging technique in the presence of off-resonance isochromats. In this case, different offsets in the range of ±20 Hz were simulated. The first six excitations are a part of the catalytic sequence that scales the longitudinal magnetization to the level achieved at steady state, and then the spoiler gradients are applied. Transverse magnetization evolves over the next 4 TRs using rf pulses with linearly increasing tip angle. There is some residual oscillation not eliminated by the catalytic sequence. The signal in the imaginary part encodes solely the region of image with oscillating $\Delta B_z$.

Figure 8:
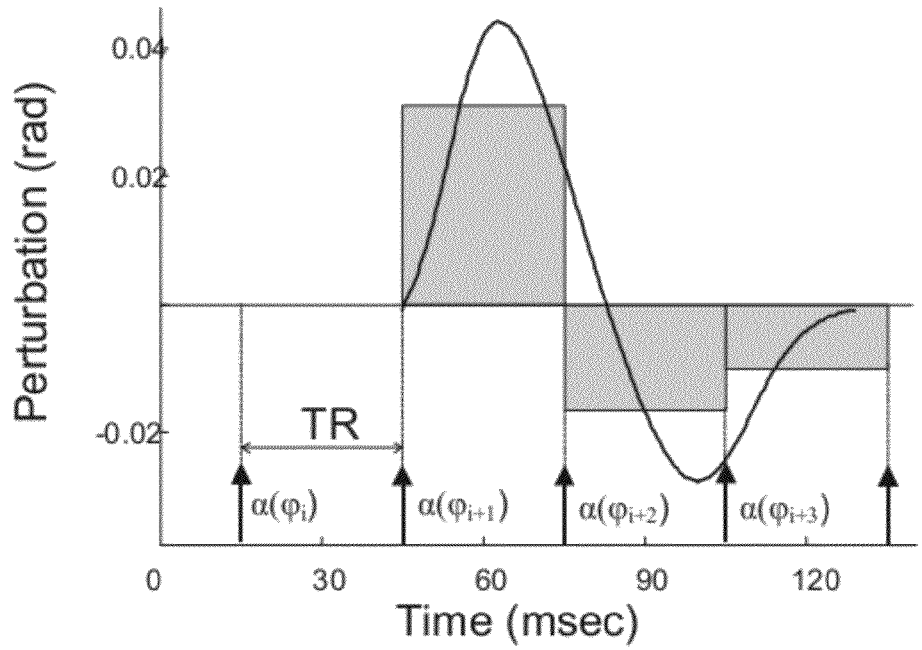
FIG. 8 is a plot illustrating an example pulse sequence and perturbation.

FIG. 8 illustrates an example RF pulse sequence and an example perturbation. The solid line represents the waveform of an example phase-perturbing factor (e.g., an electric current) that is locked to RF pulses. The RF pulses are represented by the arrows in the plot. In the example, RF pulses are phase-cycled (e.g. $-\alpha$ and $\alpha$). The illustrated example uses four-state MABSS, meaning that the pulse sequence, in the presence of the magnetic field perturbation, causes the magnetization of a sample to assume four different steady states during each of a plurality of sequential time periods. The continuous line represents the time course of the spin phase perturbing factor. The spin-phase perturbing factor may be a magnetic field perturbation, causing local changes ($\Delta B_z$) to the z-component of the magnetic field. Example spin-phase perturbing factors include neuronal current dipoles and others. It is assumed that the waveform is repeated periodically many times so that magnetization evolves into multiple steady states. The grey bars represent the mean perturbation value between each two succeeding excitation (RF) pulses. In this example there are N=4 distinct mean values. These mean values are proportional to the integral of $\Delta B_z(i)$ over an interval $\tau$=[0,TR].

The pulse sequence is configured to generate, in the presence of a magnetic field perturbation, a sequence of multiple different steady states of magnetization in the sample during each period of the pulse sequence. A magnetic resonance signal acquired from the sample can be processed to identify characteristics of the magnetic field perturbation in the sample. In some implementations, processing the signal to identify characteristics of a magnetic field perturbation in the sample includes processing the signal to identify characteristics of an electric current in the sample.

In some cases, the rf pulses that are synchronized with the time-dependent perturbations to the principal magnetic field to measure a magnetic resonance signal in a steady state to obtain a long phase integration time. In this case, the measured magnetic resonance signal is processed to uncover a weak periodic or quasi-periodic signal carried by the measured magnetic resonance signal.

Figure 9:
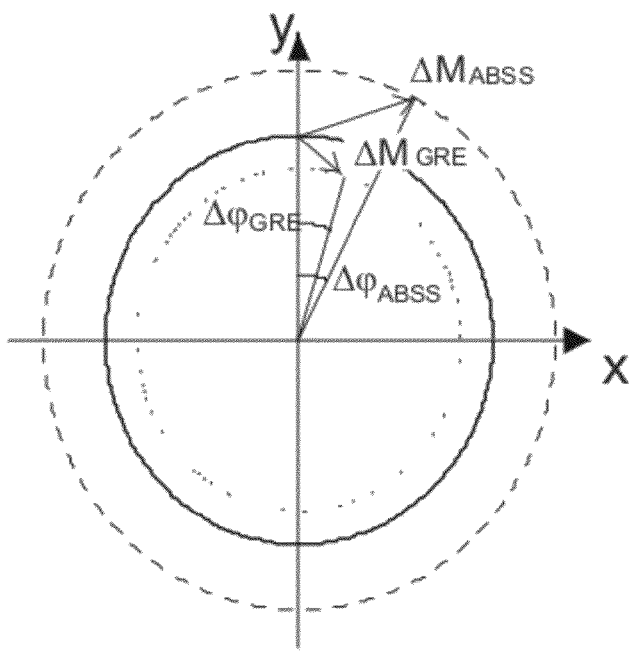
FIG. 9 is a plot comparing magnetization generated using two different pulse sequences.

FIG. 9 illustrates an example comparison of DABSS signal to gradient recalled echo (GRE) imaging. In an example GRE experiment the current-induced perturbation of the magnetic field $\Delta B_z$ has the greatest impact on the signal phase and a lesser effect on the signal magnitude attenuation due to spin dephasing. In an example ABSS experiment both phase and magnitude are affected substantially, and the direction of the effect depends on the static off-resonance. A natural method of comparison of the two signals is to use the magnitude of the modulation of the complex signal (indicated by the arrows).

The resulting magnetization in FIG. 9 (and MR signal) can be calculated as follows. Using matrix notation, the T1 and T2 relaxation can be represented by multiplying a magnetization vector M by C(t)=exp(-t/T), where T=diag (T2,T2,T1), and adding a vector $D(t)=(I-C(t))|0\ 0\ M_z|^T$. Here I is the 3×3 identity matrix and diag is a diagonal matrix. Then it can be shown that magnetization for the two alternating steady states at the echo time $\tau$=TR/2 are:

$$M_{SS1}=(I-A_1)^{-1}B_1,$$

$$M_{SS2}=(I-A_2)^{-1}B_2,$$

with $$A_1=E(\tau,\nu_1,\alpha)E(TR,\nu_2,-\alpha)C(\tau)$$

$$B_1=[E(\tau,\nu_1,\alpha)E(TR,\nu_2,-\alpha)+I]D(\tau)+E(\tau,\nu_1,\alpha)D(TR)$$

$$A_2=E(\tau,\nu_2,-\alpha)E(TR,\nu_1,\alpha)C(\tau)$$

$$B_2=[E(\tau,\nu_1,-\alpha)E(TR,\nu_1,\alpha)+I]D(\tau)+E(\tau,\nu_2,-\alpha)D(TR)$$

where $\nu_i=2\pi(\Delta f+\delta f_i)$ is the angular velocity of the free precession for the i-th steady state and $E(t,\nu,\alpha)=R_z(t\nu)C(t)R_x(\alpha)$.

FIG. 10 shows example transverse magnetization magnitudes (relative to initial magnetization $M_0$) and phases for the two alternating steady states as a function of static off-resonance $\Delta f$ for RF-locked alternating current that induces phase rotation alternating between $\delta f$=0 and $\delta f$=0.5 degrees. The difference between the two steady states is preserved over a range of off-resonances centered on 0. For TR=30 milliseconds, the period of the phase spectrum is 1/TR≈33 Hz, and thus the two states are separated significantly over ~8 Hz (±90 degrees; see FIG. 10B).

Figure 10A:
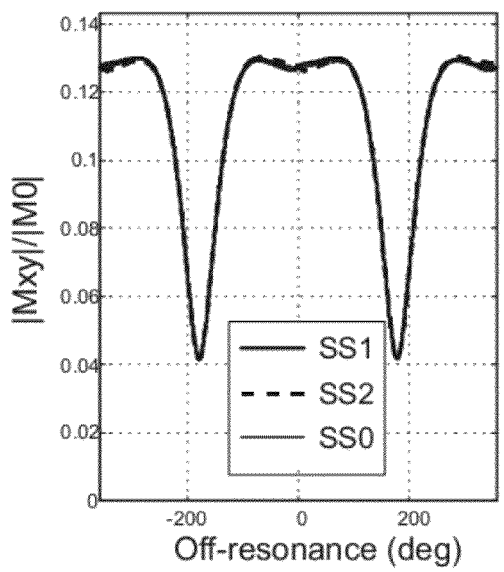
FIGS. 10A-B are plots illustrating the amplitude of an example simulated magnetic resonance signal.
Figure 10B:
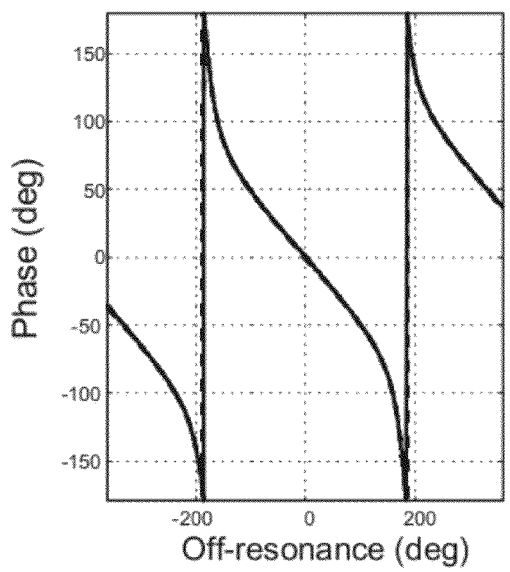
Figure 10C:
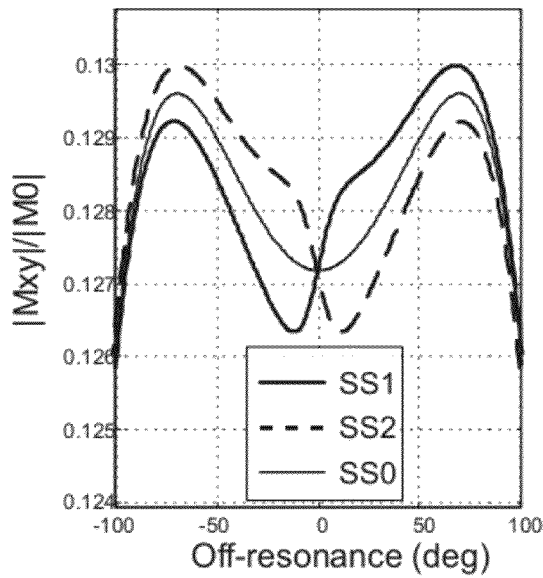
FIG. 10C-10D are plots illustrating the phase of an example simulated magnetic resonance signal.
Figure 10D:
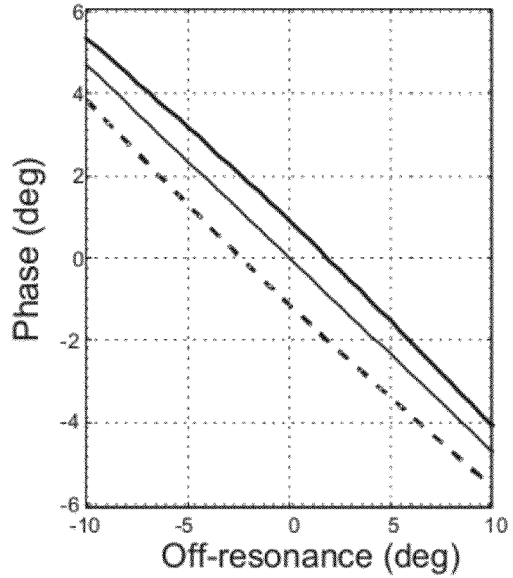

FIGS. 10A, 10B, 10C, and 10D illustrates data from an example Bloch simulation of the amplitude (FIGS. 10A and 10B) and the phase (FIGS. 10C and D) of transverse magnetization as a function of the spin precession ("phase spectrum") due to static off resonance for the two steady states induced by $\delta f$=0.5 degrees every other TR. Sequence parameters used in the example are specified as follows: T1/T2/TR/TE=1300/110/30/27 ms. Transverse magnetization (Mxy) is calculated at TE. In FIGS. 10A and 10C, off-resonance function is plotted for two full periods of phase precession. In FIGS. 10B and 10D, the same off-resonance functions plotted on a finer scale (±100 and ±10 degrees). As seen in FIGS. 10A-B the amplitudes of the two steady states demonstrate mirror symmetry. The black broken line shows a non-oscillating steady state. As seen in FIGS. 10C-D, phase functions are aligned to reveal the phase difference due to $\delta f$.

The MABSS magnetization for a spin isochromat can be calculated by extending the propagation approach presented above for the ABSS, but in the case of MABSS, the complex signal (or magnetization) as a function of off-resonance is evaluated for N steady states:

$$M_{SSi}=(I-A_i)^{-1}B_i,$$

with $$A_i=E(\tau,\phi_i,\alpha)E(TR,\phi_j,\alpha)E(TR,\phi_k,\alpha)E(TR,\phi_l,\alpha)E(\tau,\phi_i,0)C(\tau)$$

$$B_i=[E(\tau,\phi_i,\alpha)E(TR,\phi_j,\alpha)E(TR,\phi_k,\alpha)E(TR,\phi_l,\alpha)+I]D(\tau)+\ldots[E(\tau,\phi_i,\alpha)E(TR,\phi_j,\alpha)E(TR,\phi_k,\alpha)+E(TR,\phi_i,\alpha)E(TR,\phi_j,\alpha)+E(\tau,\phi_i,\alpha)]D(TR)$$

where $E(t,\phi,\alpha)=R_z(t\phi)C(t)R_x(\alpha)$, and $\phi_i=2\pi(\Delta f+\delta f_i)$ is angular velocity of spin free precession given phase perturbation $\delta f_i$ by applied current during the i-th steady state. The indices are as follows: j=mod(i+2,N)+1, k=mod(i+1,N)+1, l=mod(i,N)+1. The magnitude and phase of MABSS magnetization in FIG. 11 have been calculated using the equations above.

Figure 11A:
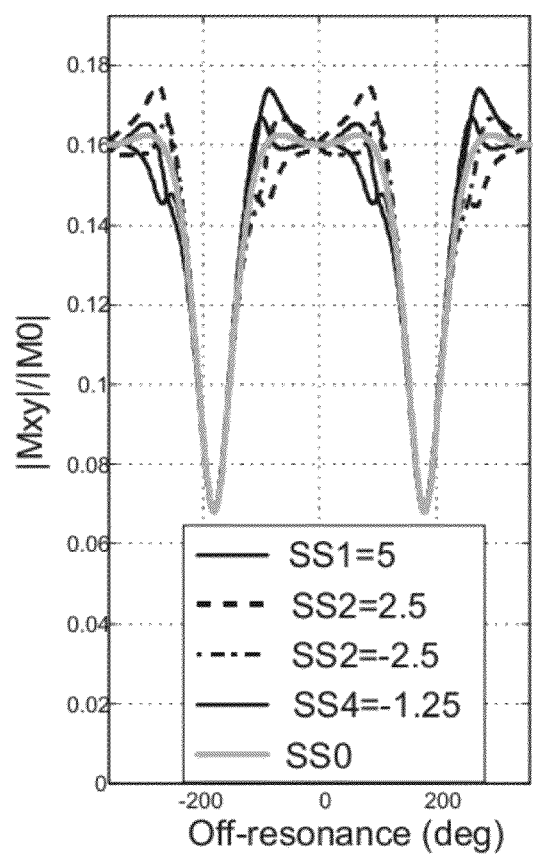
FIG. 11A is a plot illustrating the amplitude of an example simulated magnetic resonance signal.
Figure 11B:
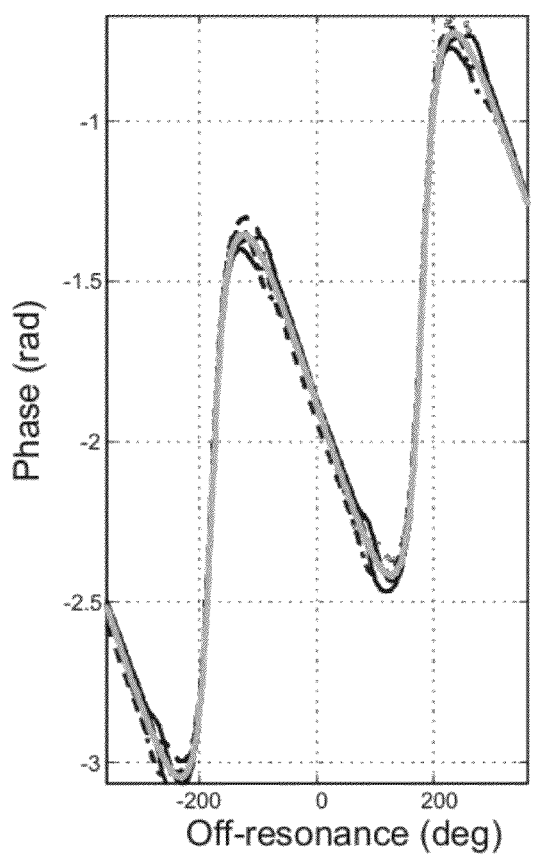
FIG. 11B is a plot illustrating the phase of an example simulated magnetic resonance signal.

In FIGS. 11A and 11B, the magnitude (FIG. 11A) and phase (FIG. 11B) of simulated transverse magnetization is plotted as a function of static off-resonance for the four steady states ($SS_i$, i=[1,4]). The example off-resonance profile is a periodic function of the off-resonance offset with a period of 1/TR Hz. Note that the complex magnetization value remains distinct throughout the full range of off-resonances, so even though at zero off-resonance the magnitude of all states is identical, and the phases differ substantially. The grey line plots the steady state in the absence of phase perturbing effects. The graphs are plotted for the phase-cycling of RF pulse using 180 degree phase advance. The simulation parameters are T1/T2/TR=1000/80/30 ms, TE=3 ms, flip angle 27 degrees, phase perturbation angle for the 4 intervals $\Delta\phi$=[5, 2.5,-2.5,-1.25] degrees.

In the example, the MABSS signal measured for each of the N states then can be used to estimate the mean perturbations for each state thus resulting in an estimate of a smoothed perturbation waveform. The MABSS phenomenon could be used for estimation of the waveform of a neural current response. Moreover, the repetition rate of such waveform can be less (e.g., less than 10 Hz) than the minimum required for the ABSS method, and potentially can bring MR-erMEG closer to the range of temporal frequencies measured using traditional EEG and MEG.

Figure 12A:
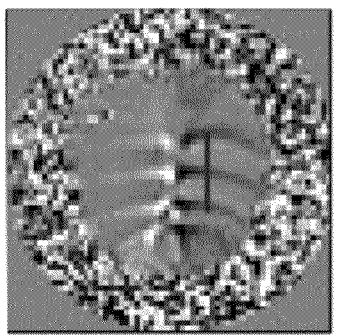
FIGS. 12A-D are example images constructed from magnetic resonance signals.

The sensitivity of an ABSS pulse sequence to alternating electric current was explored using an agar phantom with relaxation properties imitating those of gray matter. An insulated copper wire was inserted in the middle of the phantom perpendicular to the principal external magnetic field $B_0$ vector of a GE 3T scanner. The range of currents explored was I=1 mA–10 uA. The magnetic field $B_z$ in the z-direction induced by a long wire falls off as an inverse function of distance x from wire as $B_z(x)=\mu_0 I/(2\pi x)$. For example, for I=0.1 mA, $B_z(4 \text{ cm})=0.5$ nT. A balanced SSFP sequence with 1-shot spiral and echo-planar readout was used (TE=3ms, TR=31 ms, FOV=120 mm, 64×64 matrix, 4 mm slice thickness). A total of 600 images were acquired during experiments using 10-100 microampere (uA) current and 1200 images were acquired for the weak currents, resulting in scan durations of 18 or 36 seconds, respectively. Such short scan durations are determined by gradient hardware limitations and scanner drift (~10 Hz drift over a period of a 5 min scan). The phase of the RF pulse was cycled using a 180 degree step. In order to explore sensitivity of the bSSFP signal to static off-resonance, a static linear gradient along the x-axis was applied (0.75 Gauss/meter), which resulted in a characteristic banding artifact (FIG. 12A). Mean difference images were calculated by subtracting odd from even images and averaging 275 difference images (number of repetitions=550, initial 50 discarded to eliminate relaxation effects). Modulation of the complex MR signal by application of the periodic current was detected in each voxel using Hotelling's T2 multivariate test.

Figure 12B:
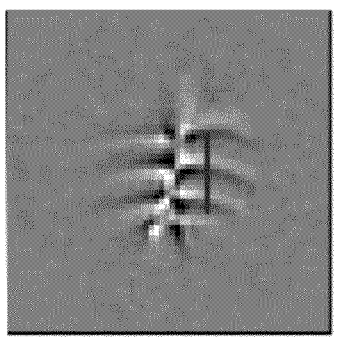
Figure 12C:
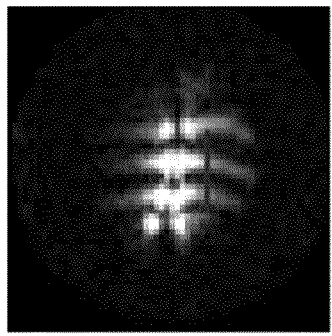
Figure 12D:
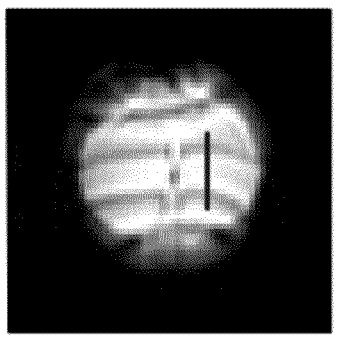
Figure 12E:
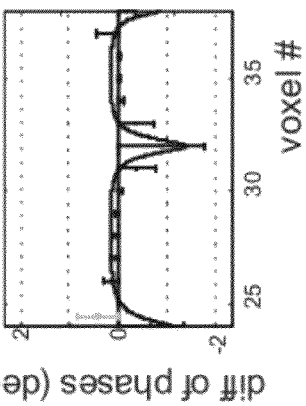
FIGS. 12E-H are plots illustrating example magnetic resonance signal intensities.
Figure 12F:
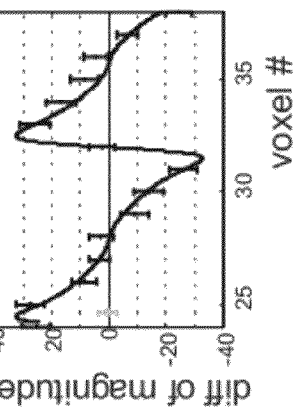
Figure 12G:
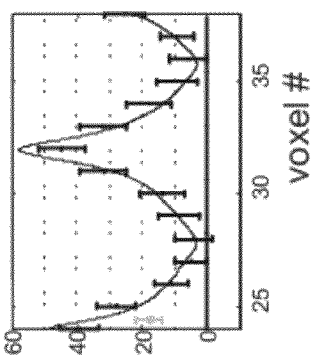
Figure 12H:
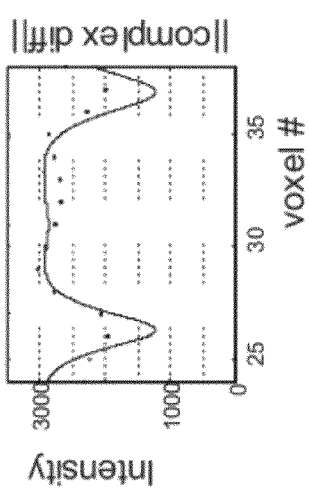

In an example implementation, a typical pattern of current-induced fluctuations is shown in FIGS. 12A-H. FIG. 12A represents a typical ABSS image of the phantom. FIG. 12B represents the magnitude of the mean complex difference between images corresponding to the two alternating steady states. FIG. 12C represents the mean difference between the magnitude images of the two alternating steady states. FIG. 12D represents the mean difference in the phase images of the two states. FIGS. 12 E-H represent measured (filled circles) and theoretical (continuous lines) off-resonance profiles. The x axis (off-resonance) of the theoretical profiles is stretched to match that of the data. The theoretical curves match the measured values very well even though the scaling factor for the y axis was not fitted to the data but calculated from the equations above and scaled by a factor given by the image intensity in FIG. 12A. The intensity profiles FIGS. 12E-H are taken 20 mm from the center, in the locations indicated by the black bar on the images of FIGS. 12A-D.

Figure 13C:
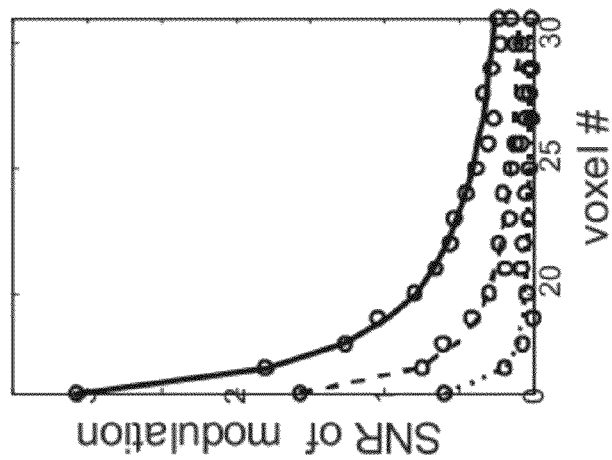
FIGS. 13B and 13C are plots comparing various aspects of the magnetic resonance signals generated using the two different pulse sequences.
Figure 13B:
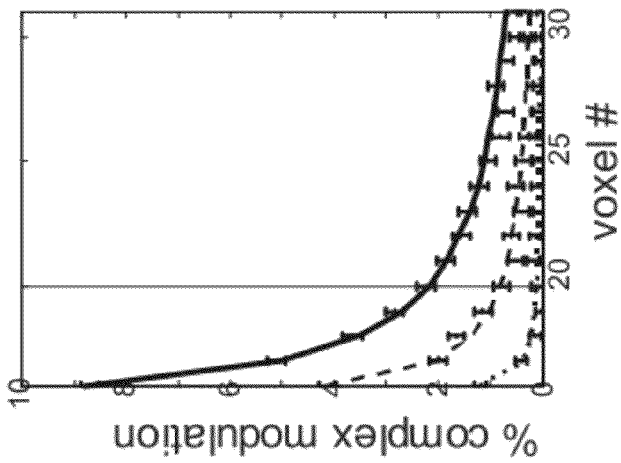
Figure 13A:
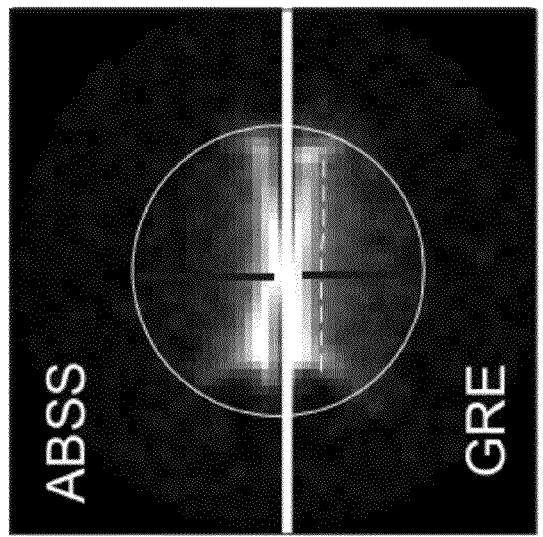
FIG. 13A is an example image constructed from magnetic resonance signals generated using two different pulse sequences.

FIGS. 13A-C show an example comparison of the current-induced signal modulation in DABSS and GRE experiments as a function of distance from the wire. FIG. 13A represents an example composite image of the average magnitude of the complex difference between the two alternating steady state images (top half) in the presence of an X-gradient (0.75 G/m) and GRE images corresponding to current-on vs. current-off intervals (bottom half), for current amplitude=100 uA; n=275; acquisition time 18 s. The white horizontal line separating the two half-images corresponds to the location of the wire. The two black vertical bars indicate pixels used for plotting profiles in FIGS. 13B and 13C. FIG. 13B represents the magnitude of complex modulation in terms of % image magnitude as a function of the distance from the wire corresponding to the vertical black bar on the modulation image of FIG. 13A. The mean and standard error of the mean (dots with error bars) for the ABSS images (TR/TE=31/27 ms) are fitted by the continuous line (the best-fitting hyperbola), for the GRE images acquired using long echo time are fitted by the broken line (TR/TE=31/27 ms), and for the GRE images acquired using short echo time are fitted by the dotted line (TR/TE=31/3 ms). The vertical line represents the cutoff distance at which modulation by current is detectible (1.5 nanotesla (nT)). FIG. 13C represents the temporal SNR of the complex modulation as a function of the distance from the wire, corresponding to the three scan protocols used for FIG. 13B.

In the GRE experiments employing 100 uA alternating current (18 second scan, N=550), the modulation pattern was detectable using Hotteling's T2 test up to 15 millimeters (mm) away from the wire (indicated by the horizontal white broken line in the lower half of FIG. 13A), corresponding to the detection limit of $\Delta B_z$~1.5 nT. By contrast, the ABSS signal was modulated according to the characteristic pattern and was reliably detectable up to the edge of the phantom (~5 cm from the wire), corresponding to $\Delta B_z$~0.5 nT. We have explored the limits of ABSS sensitivity to periodic currents by applying 10 and 20 uA currents to the phantom. Application of 10 uA alternating current in ABSS experiments resulted in detection (p=0.05) of modulation in 33% of 18 second scans (5 out of 15). In the five successful scans the mean detected minimum $\Delta B_z$ was 159±82 picotesla (pT). In the experiment employing 20 uA current and a 36 second (s) scan (N=1150), the modulation was detectable at the distance of ~30 mm, corresponding to $\Delta B_z$~150 pT, consistent with the 10 uA experiments. In the examples presented, DABSS offers higher SNR for detection of weak spin phase-perturbing factors such as weak currents as compared to previously used methods.

FIGS. 14A-E represent example data from Bloch simulation of low-pass filtered off-resonance profiles. FIG. 14A plots the MABSS (N=4 steady states) signal and FIGS. 14B-E plot the signal deviation from the mean of the four steady states as a function of off-resonance. FIGS. 14F-J are example images obtained using the MABSS sequence, and FIGS. 14K-O are example intensity profiles obtained using the MABSS sequence. FIGS. 14F-J plots an average MABSS image at steady state and the modulation patterns corresponding to the four steady states. The vertical stripes are banding artifacts introduced by a linear X gradient that was applied in order to generate linearly-varying off-resonance. The horizontal line in the middle of the images is the location of the wire. The horizontal line below the central line indicates the site for the profiles depicted in FIGS. K-O. The experimental profiles follow those predicted by the theory rather closely.

Figure 15:
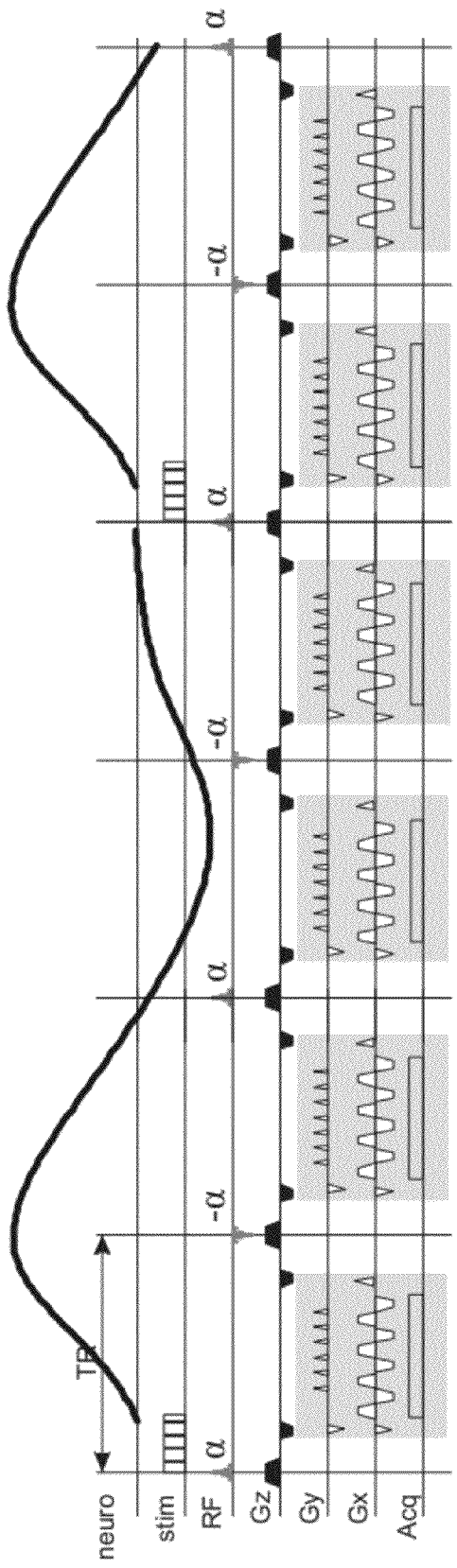
FIG. 15 is a plot illustrating various aspects of an example magnetic resonance experiment.

FIG. 15 illustrates an example MABSS experiment with a segmented (multishot) EPI acquisition. First, a k-space subspace for the N=4 MABSS states are acquired sequentially and then the pulse sequence moves to acquire the next k-space subspace. The acquired k-space lines need to be sorted according to the steady state before the image reconstruction step. The top horizontal line represents the evoked neuronal population response by the stimulus (second line). The RF pulse (third line) is phase cycled by 180 degrees and the slice-select gradient $G_z$ (fourth line) is completely counter-balanced across TR. The shaded rectangle marks the multi-shot EPI acquisition portion of the pulse sequence. Any other standard acquisition sequence can be used here provided all the gradients are balanced over TR interval (i.e. net gradient area equals to zero).

Figure 16A:
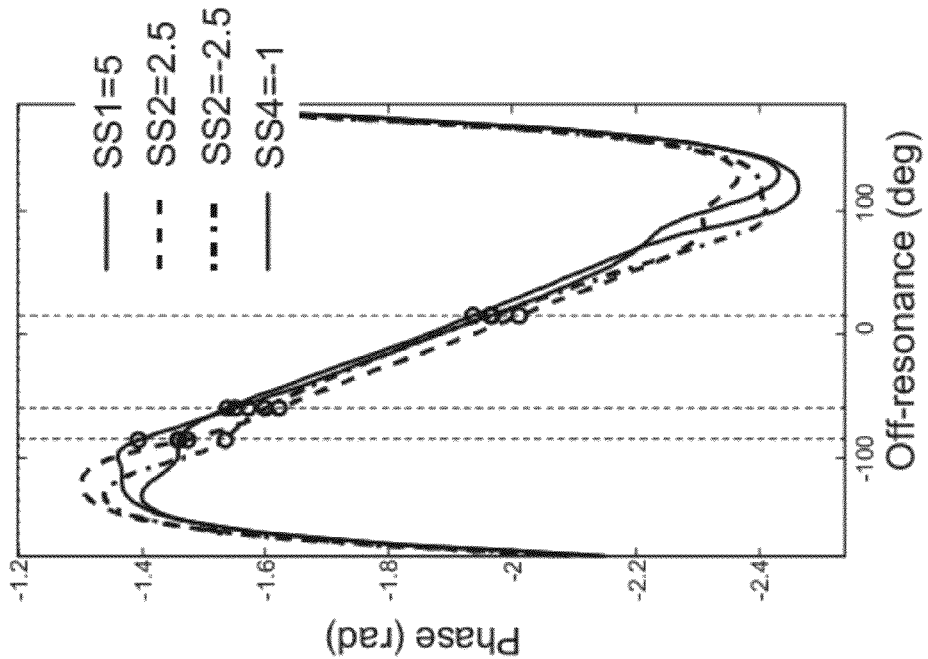
FIG. 16A is a plot illustrating the amplitude of an example simulated magnetic resonance signal.
Figure 16B:
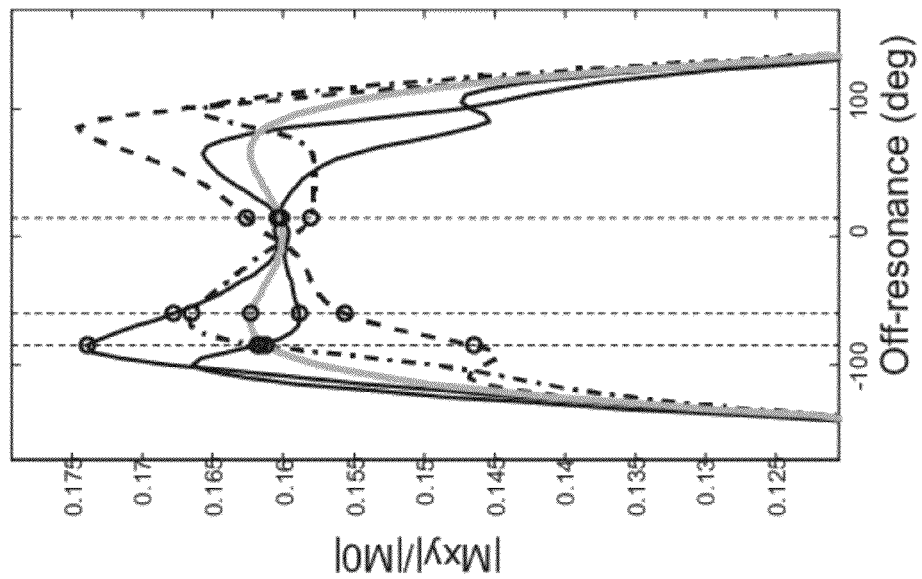
FIG. 16B is a plot illustrating the phase of an example simulated magnetic resonance signal.

FIGS. 16A and 16B illustrate an example performance of the Nedler-Mead simplex optimization method when solving for the discretized phase-perturbing waveform. Black lines correspond to the magnitude (FIG. 16A) and phase (FIG. 16B) of the MABSS off-resonance profiles at steady state. The grey lines correspond to off-resonance profile of the bSSFP (no-perturbations) steady state. The simulation parameters are as in FIG. 9. The open circles represent the estimates of MABSS and bSSFP complex-valued measurements taken at three different off-resonances (marked by vertical broken lines). The open circles lay nearly exactly on the simulated "true" off-resonance profiles, indicating high accuracy of the optimization algorithm.

The current (or other spin phase-perturbing factor) waveform can be estimated from the complex-valued measurements of MABSS signal at the N steady states, since this is a well-posed problem. From the equations above, it follows that the complex-valued MABSS signal vector $S_{SS}=[S_{SS1},\ldots,S_{SSN}]^T$ is a function of multiple parameters $$S_{SS}=F(\delta\Phi,\Delta f,TR,TE,T1,T2,\alpha),$$

with only N+1 unknowns: the static off-resonance offset $\Delta f$ and the N-vector of phase perturbations $\delta\Phi=[\delta f_1,\ldots,\delta f_N]^T$. This equation can be solved for $\Delta f$ and $\delta\Phi$ using numerical optimization methods, since the complex-valued MABSS measurements provide redundant information. In order to improve stability of the solution, a measurement in the absence of perturbations $S_{SS0}$ can be also included. Additional effective optimization scenarios involve inclusion of measurements at several voxels with varying off-resonance offset $\Delta f$ but fixed perturbation vector $\delta\Phi$.

For purposes of the method demonstration the Nedler-Mead simplex optimization method is used to solve for a scenario whereby (1) 4-state MABSS measurements are given from 3 voxels with variable unknown $\Delta f$ and identical N perturbations and (2) the signal has also been measured for a steady state without perturbations. It is also assumed that TR, TE, T1, T2, and $\alpha$ are known. FIGS. 16A and 16B plot example off-resonance profiles of the MABSS steady state magnetization for a phase-perturbing waveform with mean values $\delta\Phi=[5,2.5,-2.5,-1]^T$ degrees (black lines) and of the bSSFP (i.e. no-perturbation steady state) magnetization (grey line).

The three columns of circles (marked by vertical dotted lines) represent MABSS and bSSFP signal values corresponding to the solution found by the optimization procedure. The fit error can be effectively reduced or minimized by selecting an approximate initial guess for the unknown values. The estimated phase perturbation values $\delta\hat{\Phi}=[5,2.5,-2.5,-1]^T$ degrees and the estimated off-resonance offsets approximate the "true" simulated within less than 0.1%. Similar high-accuracy results can be obtained when estimating perturbation values for MABSS steady states produced using small phase perturbation values, that might be found in the brain, e.g. with $\delta\Phi=[0.5,0.25,-0.25,-0.1]^T$ degrees, and using only a single offset value (corresponding to independent processing of each voxel). Measurement of the no-perturbation steady state (bSSFP signal) is not necessary for obtaining good fits, even though it may provide a good point of reference for interpreting MABSS data.

In the light of high accuracy of the waveform solution by means of numeric optimization, a main source of error in the proposed method is the discretization error. The discretization error may be reduced by reducing TR and thus increasing N, but at the expense of the magnitude of MABSS steady state modulation and hence at the expense of SNR. This tradeoff may be further optimized for specific scenarios. For example, in neuronal population responses, TR might be optimized by recording EEG/MEG signals and tailoring TR to match the waveform and latency of these signals.

The second source of error in the example MRI data obtained using MABSS is spatial smearing due to a non-ideal point spread function (PSF). Thus for the real MRI data the waveform estimation would be performed using the equations above corrected for such spatially convolutive effect of the PSF.

The described techniques can be used to detect periodic variations in spin phase-perturbing factors such as magnetic field and quasi-periodic variations derived from periodic sequences, and to estimate the waveforms of such periodic variations. Periodic activations have been successfully used in electro- and magnetoencephalographic investigations of cognitive brain functions (frequency tagging approach). Because the brain is a source of a multitude of endogenous rhythms, ABSS techniques in conjunction with RF excitation synchronization via in-scanner EEG might be potentially capable of revealing sources of these endogenous oscillations.

The ABSS method potentially can be applied in imaging weak oscillating magnetic fields with high sensitivity and spatial resolution. Thus it potentially can be applied in MR magnetoencephalography. Thus, this method can potentially enhance the resolution of brain imaging based on measurement of magnetic fields (MEG), and improve functional brain MR imaging technologies by adding to the existing set of functional MR contrasts (such as BOLD and cerebral blood flow) a method to directly monitor electric activity of the brain. Thus, the disclosed processes would be applicable in many commercial domains in which present day MEG and fMRI is used, including brain (and other electrogenic organ) research and diagnostics of neurological and psychiatric conditions.

Figure 17:
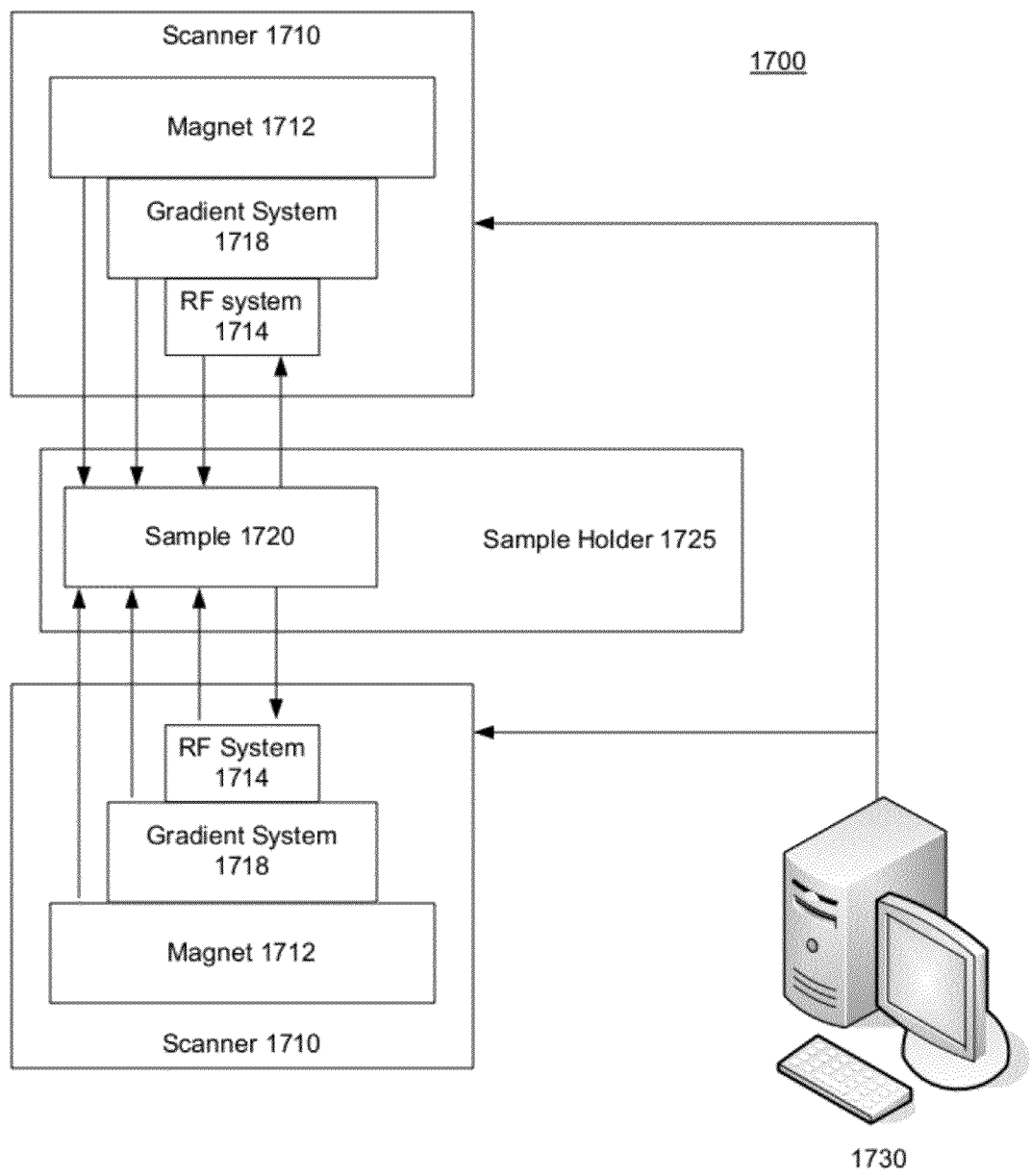
FIG. 17 is a diagram illustrating an example magnetic resonance imaging system.

Techniques as disclosed in this specification can be implemented using an MRI system 1700 as illustrated in FIG. 17. The MRI system 1700 can be implemented using any one of various commercially available MRI scanners, such as a 3 Tesla scanner from GE. The MRI system 1700 includes a scanner 1710, a data processing apparatus 1730 and a sample holder or table 1725 for holding a sample 1720. The scanner includes a main magnet 1712, a gradient system 1718 and an rf system 1714. The main magnet 1712 is designed to provide a substantially constant, homogeneous external magnetic field. The gradient system 1718 may include multiple gradient coils designed to provide magnetic field gradients (e.g., gradients along axes defined by Cartesian or polar geometries) used to acquire image data of a desired slice by generating a phase encoding and/or slice-selecting magnetic field. The rf system 1714 may include an rf transmit coil and a separate rf receive coil designed to separately transmit and receive rf pulses. Alternatively, the rf system 1714 may include an rf transceiver that has a single rf coil for receiving and for transmitting rf signals. For example, a close-fitting smaller coil may improve image quality when a small region is being imaged. Further, various types of coils that are placed around specific parts of a body (e.g., the head, knee, wrist, etc.) or even internally can be implemented depending on the sample and imaging applications. The rf system 1714 can further include an rf synthesizer (not shown), a power amplifier (not shown), and various other hardware components.

The MRI system 1700 is designed to perform the techniques disclosed in this specification. In particular, the MRI system 1700 can implement the disclosed pulse sequences based on ABSS techniques, as well as other types of pulse sequences. The rf system 1714 is designed to apply to a sample 1720 a pulse sequence, such as the pulse sequences described herein. The gradient system 1718 applies magnetic field gradients and magnetic readout gradients. The data processing apparatus (e.g., a computer) 1730 is designed to receive and process the acquired data to obtain desired images and information.

Figure 18:
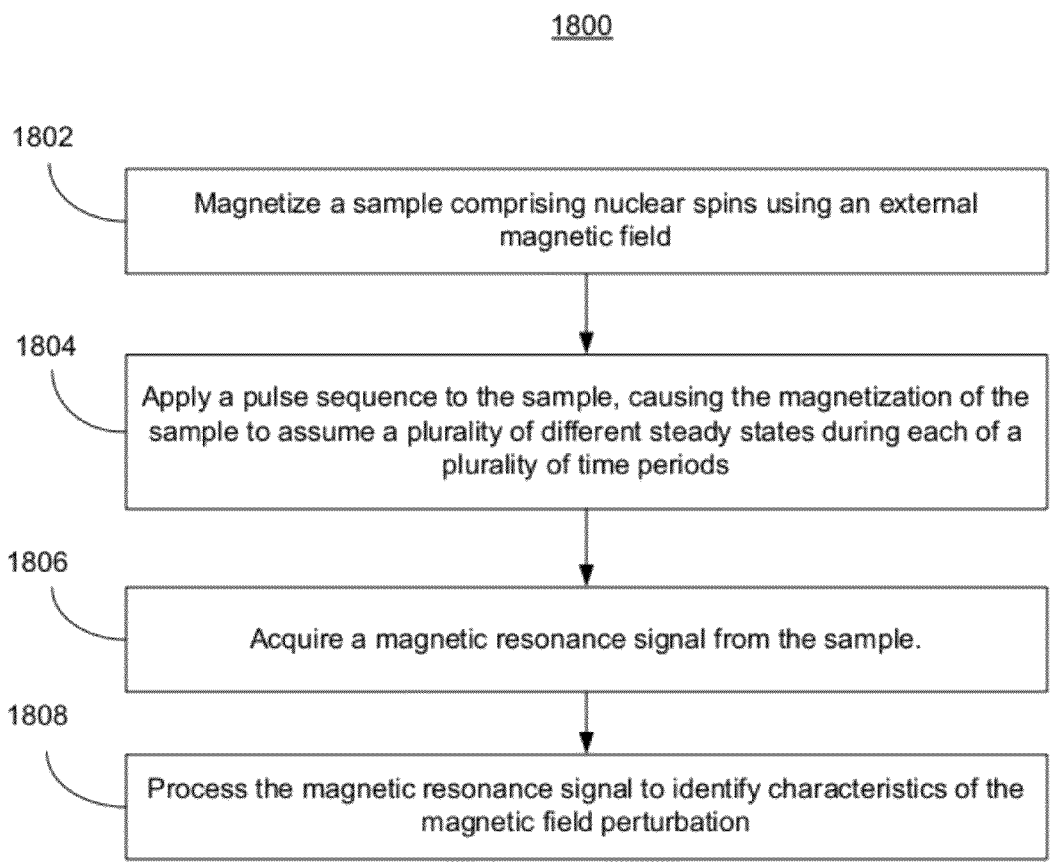
FIG. 18 is a flow chart illustrating an example process for magnetic resonance imaging.

FIG. 18 is a flow chart illustrating an example process 1800 for magnetic resonance imaging. At 1802, a sample comprising nuclear spins is magnetized using an external magnetic field. At 1804, a pulse sequence is applied to the sample.

The pulse sequence includes multiple magnetic rf pulses and multiple recovery times. During the recovery times, in some implementations, no rf pulses are applied to the sample. However, in other cases, rf pulses are applied during one or more of the recovery times. The pulse sequence may also include gradients. For example, a pulse sequence may include a time sequence of gradients that have zero integral, for generating balanced steady states.

The pulse sequence can cause the sample magnetization, or a component of the sample magnetization, to transit among multiple steady states (e.g., two, three, or more steady states) during each of a plurality of time periods. For example, the magnetization may assume a first steady state after a first rf pulse during a first time period, and the magnetization may assume a second steady state after a second rf pulse during the first time period. For example, when k number of steady states are used, the magnetization may assume, after the period of transition into the equilibrium, a first steady state after the N*k+1th rf pulse during the Nth time period, and the magnetization may assume a second steady state after a N*k+2nd rf pulse during the Nth time period. Then, during a subsequent second time period, the magnetization may again assume the first steady state and then the second steady state.

The pulse sequence is synchronized with a magnetic field perturbation. For example, the pulse sequence may be made up of multiple repetitions of a shorter pulse sequence (e.g., a +α pulse followed by a −α pulse repeated many times). The period of the shorter pulse sequences may correspond to a period, a fraction of a period, or an integer number of periods of the magnetic field perturbation. The magnetic field perturbation may be periodic or quasi-periodic. The rf pulses may be synchronized to the period of the magnetic field perturbation.

The perturbation may interact with the sample magnetization. For example, the magnetization in one or more of the steady states may interact with the magnetic field perturbation. The net effect of the interaction repeated over the plurality of sequential time periods may effectively amplify an effect of the interaction that occurs during a single time period. The interaction may change a phase of the magnetization, for example, during at least a portion of each of the plurality of time periods. The phase may be determined by a local magnitude of the magnetic field perturbation. In some cases, the interaction repeated over the plurality of sequential time periods causes the magnetization to accumulate a phase that is the additive sum, or the integral, of the phases acquired during the individual time periods.

In some implementations, the magnetic field perturbation is generated at least in part due to an electric current in the sample. For example, the sample may be a brain of a human or another organism, and the electric current may be a neuronal current in the brain.

In some cases, the magnetic field perturbation is stimulated. Stimulating the magnetic field perturbation may include mechanically perturbing the sample. Stimulating the magnetic field perturbation may include stimulating the magnetic field perturbation with a frequency to which the pulse sequence is synchronized. In some cases, the sample includes at least a portion of a living organism, and stimulating the magnetic field perturbation includes presenting a sensory stimulus to the living organism. The sensory stimulus may include visual, audio, or other types of stimuli.

After or during the application of the pulse sequence, a magnetic resonance signal is acquired from the sample (1806). Next at 1808, the magnetic resonance signal is processed to identify characteristics of the magnetic field perturbation. For example identifying characteristics may include obtaining or extracting the characteristic based on analysis of the signal. The characteristic may include, for example, at least one of a location of the magnetic field perturbation, a magnitude of the magnetic field perturbation, or a waveform of the magnetic field perturbation. In some cases, when the sample includes an organism, processing a measured magnetic resonance signal includes identifying a mechanical property of a tissue of the organism. The organism may be a living organism, in some cases. For example, the tissue may be mechanically stimulated by vibrations, and processing the MR signals may include generating an image of a vibration response pattern in the tissue. The tissue may be, for example, a tumor.

The process 1800 can be used to extract a diffusion rate in the sample. In such a case, the perturbation may be generated by the gradient system. In some cases, the sample comprises a blood vessel, the method further comprising processing a measured magnetic resonance signal to identify a flow rate of fluid (e.g., blood) along the blood vessel. For example, the method may be used for angiography applications.

The described processes may be used to detect periodic variations in spin-phase perturbing factors such as magnetic field and quasi-periodic variations derived from periodic sequences. The described processes may also be used to estimate the waveforms of such periodic variations. Periodic activations have been successfully used in electro- and magneto-encephalographic (i.e., EEG and MEG) investigations of cognitive brain functions (e.g., using a frequency tagging approach). Because the brain is a source of a multitude of endogenous rhythms, ABSS-based techniques in conjunction with rf excitation synchronization via in-scanner EEG might be potentially capable of revealing sources of these oscillations.

ABSS-based techniques may be applied in imaging weak oscillating magnetic fields with high sensitivity and spatial resolution. Such techniques may be applied in MR magnetoencephalography, for example, to enhance the resolution of brain imaging based on measurement of magnetic fields (MEG), and enhance functional brain MR imaging technologies by adding to the existing set of functional MR contrasts (such as BOLD and cerebral blood flow) a process to directly monitor electric activity of the brain. Thus, ABSS-based techniques would be applicable in many commercial domains in which present day MEG and fMRI techniques are used, including brain (and other electrogenic organs) research and diagnostics of neurological and psychiatric conditions.

Conventional BOLD fMR brain imaging offers a window of limited spatio-temporal bandwidth for monitoring dynamics of neuronal activity. Typical implementations of conventional techniques may not monitor the relevant temporal resolution of 10-100 ms. Direct measurement of neuronal currents using neuronal current MRI (ncMRI) has a potential of affording such temporal resolution, but is may be limited by low magnitude of ncMRI signal. Smart MRI contrast agents (SCAs) can track correlates of rapid neuronal activity, such as extracellular $Ca^{++}$ concentration. MR signal generation mechanisms of ncMRI and SCA fMRI share features that can be exploited by means of balanced SSFP. ABSS MRI techniques for ncMRI. The ABSS MRI technique can be extended for high temporal resolution measurements of periodic waveforms of spin phase-perturbing factors that correlate with neuronal activity. Such an approach may allow high sensitivity and stability in the presence of injected noise.

Some conventional techniques for MRI of brain function utilize variations in deoxyhemoglobin concentration in cerebral parenchyma that reflect underlying neuronal activity indirectly through neurovascular coupling, which depends on many physiological parameters. The blood oxygenation level dependent (BOLD) signal evolves over seconds, while the temporal scale relevant for neuronal activity ranges from 10-100 ms. It may be possible to detect neuronal currents directly by means of MRI (ncMRI) since minute magnetic fields generated by electrical neuronal activity can perturb proton spin phase. Indeed, in situ (in voxels acquired using MRI) the peak magnetic field strength adjacent to neuronal current dipoles yields $\Delta B=10^{-9}-10^{-10}$ T=0.1-1 nT. An extended homogenous dipole covering a 3×3×2 mm volume and generating the same 10 nTm effective point dipole would afford the maximum voxel-averaged $\Delta B=0.17$ nT. Similar estimates were obtained in calculations based on realistic neuron morphology. Such estimates are well within the sensitivity of contemporary MR scanners.

Smart MRI contrast agents (SCA) may offer an answer to the problem of the weak signal strength generated by neuronal currents. $Ca^{++}$ concentration-sensitive SCAs may be capable of boosting rapidly varying correlates of local neuronal activity, such as extracellular $Ca^{++}$ concentration. Such $Ca^{++}$-sensitive MRI SCAs are based on observation that $Ca^{++}$ concentration in the extracellular space ($[Ca^{++}]_e$) varies by as much as 30% as a consequence of neuronal activity (from ~1.2 mM in resting state to 0.8 mM during intense activation). Such $Ca^{++}$ depletion occurs mostly as a consequence of action potential back-propagation along dendritic membranes replete with several types of voltage-sensitive $Ca^{++}$ channels. Depending on dendrite density and geometry, variations of $[Ca^{++}]_e$ can reach up to 100% within a time interval of order 1 ms. Such synaptic activity-related $[Ca^{++}]_e$ fluctuations are suited to act as a marker signal for an active volume of neural tissue at a millisecond temporal scale. An example synthesized Gd-DOPTRA SCA is selective exclusively to $Ca^{++}$ (over competing $Mg^{++}$) and sensitive to $[Ca^{++}]$ with a T1 relaxivity response of 100% over $Ca^{++}$ concentration range of 0-1.5 mM. Relaxivity changes in an artificial extracellular matrix can be as high as 25%. An example Gd SCA that uses modified EGTA chelators may have similar results. These SCAs, in a solution mimicking extracellular brain fluid and at 37° C., exhibit a change in T1 relaxivity as high as 10%, as $[Ca^{++}]_e$ varies within the relevant range of 0.8-1.2 mM.

While Gd-based compounds can be used as T1 contrast agents due to their ability to shorten T1 relaxation time, these same contrast agents can to a lesser degree shorten T2 relaxation time and potentially induce shifts in the proton resonance frequency, and thus act as bulk magnetic susceptibility (BMS) contrast agents. For example, Gd-DOTA application (5 mM) can result in a resonant frequency shift of 10 Hz at 1.5 T. Therefore, effects of Gd-based SCAs can be studied at a fast temporal scale by tapping into their BMS property using frequency-sensitive pulse sequences, such as balanced SSFP. Balanced SSFP is also sensitive to T2 variations induced by such SCAs. However, in some instances, in order to maximize the amplification of signals correlating with neuronal activity at the fine temporal scale, dedicated smart contrast agents need to be synthetized that substantially change their resonant frequency as a consequence of binding to Ca++, akin to resonant frequency changes in oxy- vs. deoxyhemoglobin.

Alternating balanced steady state MRI can afford contrast-to-noise ratio (CNR) for spin phase-perturbing factors (i.e. factors that affect net $B_z$, and result in $|\Delta B_z|>0$) that is superior to that of traditional GRE and SE fMRI. Balanced SSFP MRI can be used to estimate temporal waveforms by means of multiple alternating balanced steady states FMRI. The MABSS technique can offer temporal SNR that surpasses that achievable with traditional rapid MRI techniques (such as single-shot pulse sequences like GRE EPI). These results are applicable for estimation of rapid neuronal activity waveforms (at temporal resolution of ~10 ms) with and without SCAS, and offer a potential of bridging the gap between FMRI and EEG/MEG.

Figure 19:
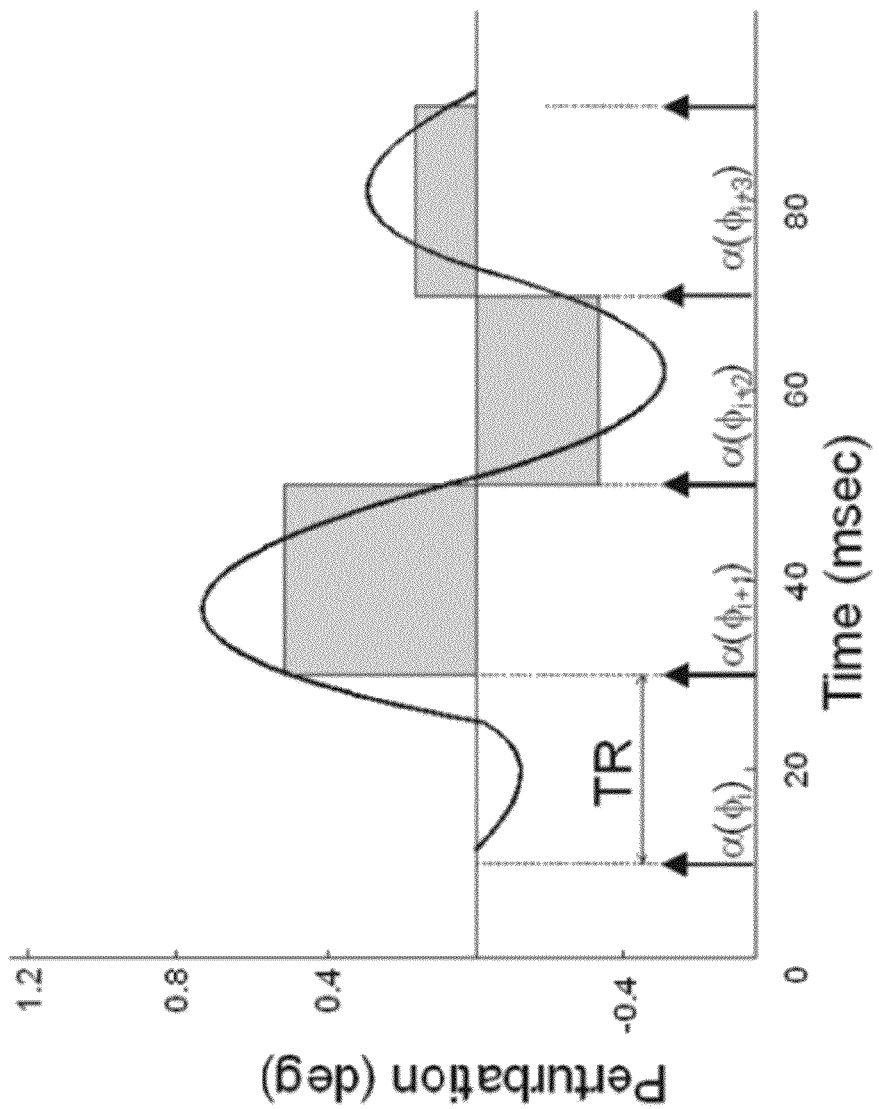
FIG. 19 is a plot illustrating an example pulse sequence and perturbation.

FIG. 19 shows an example of using the mABSS technique. The continuous line represents the time course of the $\Delta B_z$ perturbing factor F in terms of the phase perturbation. It is assumed that the waveform of duration $T_w=N \cdot TR \leq T2$ is repeated periodically so that magnetization evolves into a steady state. The grey bars represent the mean perturbation value between each two succeeding excitation (RF) pulses (plotted as arrows below). In this example, there are N=4 distinct mean values. These mean values are proportional to the integral of $\Delta B_z(i)$ over an interval $\tau=[0,TR]$.

In the example, spin phase-perturbing periodic signals are used to generate multiple alternating balanced steady states by locking a train of N rf pulses in phase to a repeated waveform of that signal: N dynamic steady states result from different exposure of transverse magnetization at each of N TRs to the spin phase-perturbing factor, as determined by the time course of the waveform (e.g., as in FIG. 19). The continuous line in FIG. 19 represents the time course of a repeated neuronal response-related factor F (induced by application of SCAs, directly by neuronal currents, and/or in another manner), and the arrows indicate timing of the RF pulses. As long as the waveform duration $T_w=N \cdot TR<T2$, the signal reaches N cyclically alternating dynamic steady states with N equal to the number of TR intervals falling within a period of the waveform. To first approximation, the degree of phase perturbation $\delta\phi_j$ is proportional to the integral of factor F over the repetition time (TR):

$$\delta\varphi_j \propto \int_0^{TR} F[(j-1) \cdot TR + \tau] d\tau$$

This results in a binned waveform representation (e.g., as shown in the shaded area in FIG. 19). Such binned waveforms can be measured as described herein. Such waveforms are applicable for measuring both ultra-weak perturbations associated with neural current-induced magnetic fields and perturbations amplified by BMS SCAs.

The mABSS magnetization for a spin isochromat can be calculated by extending the propagation approach. Using matrix notation, the T1 and T2 relaxation can be represented by multiplying the initial magnetization vector $M_0$ by $C(t)=\exp(-t/T)$ where $T=\text{diag}(T2,T2,T1)$, and adding a vector $D(t)=(I-C(t))[0\ 0\ M_z]^T$. Here I is the 3×3 identity matrix and diag is a diagonal matrix. Spin precession by an angle $\phi$ is represented by a rotation matrix $R_z(\phi)$ about the z axis; likewise the RF excitation effect corresponding to flipping magnetization around x axis by an angle $\alpha$ (with a fixed RF phase) is given by the rotation matrix $R_x(\alpha)$. For the simplified case of an RF pulse of negligible duration, the mABSS magnetization vector for N steady states SSi at time TE as a function of off-resonance frequency $\Delta f$ is given as:

$$M_{SSi} = (I - A_i)^{-1} B_i$$

with $$A_i = \left(\prod_{j=N+1}^{2} E_{ij}\right) R_z(\tau_1 \varphi_i) \cdot C(\tau_1),$$

and $$B_i = \sum_{l=2}^{N+1} \left(\prod_{j=N+1}^{l} E_{i,j}\right) \cdot D(\tau_{l-1}) + D(\tau_{N+1}),$$

where $$E_{i,j} = R_z(\tau_j \varphi_k) C(\tau_j) R_x(\alpha_k),$$

$$k = \text{mod}(i + j - 2, N) + 1$$

is the state indexing function;

$$\varphi_i = 2\pi \Delta f + \delta \varphi_i$$

is the free precession rate given off-resonance $\Delta f$ and the phase perturbation $\delta \varphi_i$ during the i-th steady state. The flip angle $\alpha_k$ alternation implements phase cycling with 180 degree step (i.e. alternates between $+\alpha$ and $-\alpha$). Time intervals $\tau_i$ may be calculated as follows:

$$\tau_i = \begin{cases} TR - TE, & i = 1 \\ TR, & i \in [2, N] \\ TE, & i = N + 1. \end{cases}$$

Propagation of solution for mABSS magnetization may require N+1 time intervals between two identical magnetization time points $t \neq n \cdot TR$ (where n is an integer). Products in the equations run backwards from j=N+1 to 2 due to non-commutativity of matrix multiplication.

Figures 23A, 23B:
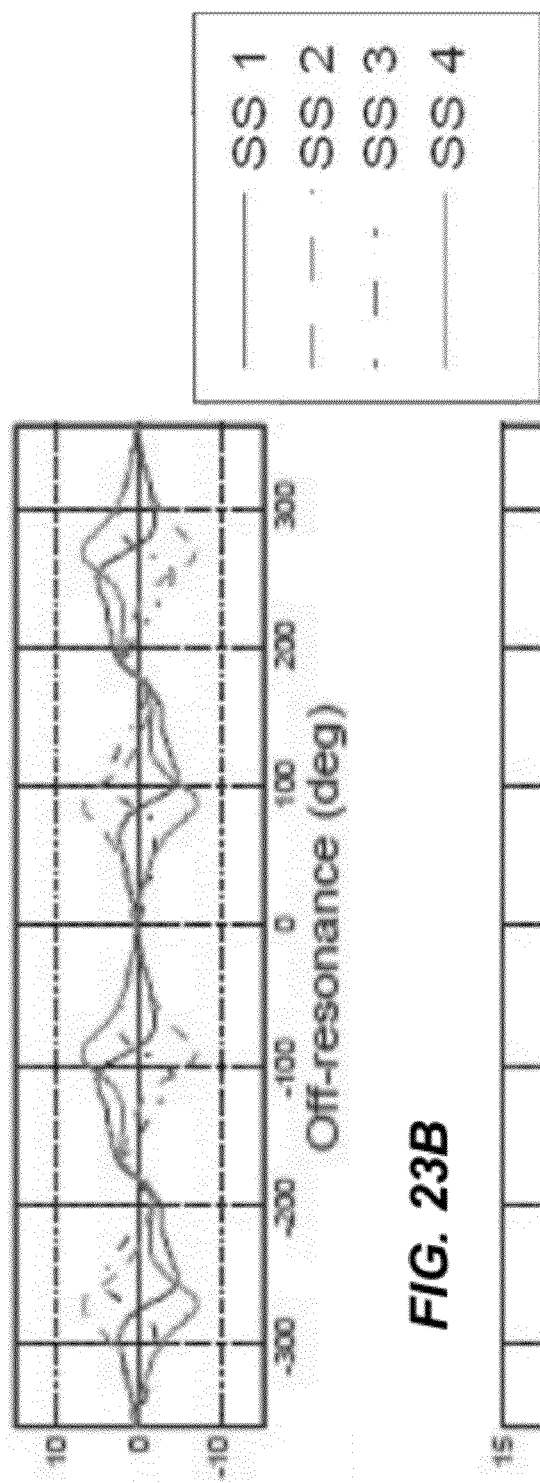
FIGS. 23A-B are plots illustrating modulation of an example simulated magnetic resonance signal.

FIGS. 20A, 20B, 21A, 21B, 22A, 22B, 23A, 23B show MABSS off-resonance profiles. FIGS. 20A-B show the magnitude, and FIGS. 22A-B show the phase of transverse magnetization as a function of static off-resonance for four steady states (SSi, i=[1,4]). The steady states are induced by the waveforms $\delta\varphi_j$[4,−2,2,−0.2] degrees/TR in FIGS. 20A-B and 21A-B. The steady states are induced by the waveforms $\delta\varphi_j$= [4,2,−2−0.2] degrees/TR in FIGS. 22A-B and 23A-B. The gray line in FIGS. 20A-B and 22A-B plots no-modulation state SS0, and other states are as indicated in the figures. The corresponding signal modulation off-resonance profiles during the 4 states (difference between SSi and the SS0) are plotted in FIGS. 21A-B and 23A-B; FIGS. 21A and 23A show $(\|SS_i\| - \|SS_0\|)/\|SS_0\|$, while FIGS. 21B and 23B show $\|SS_i - SS_0\|/\|SS_0\|$. Simulation parameters are: T1/T2/TR=1000/80/30 ms, TE=27 ms, flip angle 27 degrees.

The magnitude and phase off-resonance steady-state profiles for the 4-state mABSS transverse magnetization in FIGS. 20A-B are calculated using the equations above for $A_i$ and $B_i$. The relatively high spin phase perturbation magnitude of greater than or equal to four degrees is used in order to stress off-resonance profile differences of the four steady states. FIG. 21A-B plots signal modulation off-resonance profiles induced by the repeated perturbation waveforms (i.e. the difference between SSi and SS0). The off-resonance profiles for all steady states shown in the example plots are affected by the state alternation ordering (states 2 and 3 are swapped in FIG. 22A,B and FIG. 23A,B as compared to FIG. 20A,B and FIG. 20A,B; c.f. FIGS. 21A, 21B, 23A, 23B).

The example Monte Carlo simulations of the evolution of mABSS magnetization and MRI data analysis were performed using Matlab (MathWorks, Inc., Natick, Mass.). MRI images of a current phantom were acquired using a 3T GE Excite scanner (short bore) at the UCSD Center for fMRI and a GE receive/transmit knee quadrature coil. A 2D balanced SSFP sequence with a 1-shot spiral acquisition (±125 KHz) with FA=27 degrees, TE=2.1 ms (spiral-out) and 27 ms (spiral-in), TR=30 ms, FOV=18 cm, 64×64 matrix and 4 mm slice thickness was used to acquire a single axial slice through the plane containing the wire inside a current phantom (see below). The RF pulse shape was a simple sinc pulse (bandwith=5 kHz), and the spiral trajectory was an Archimedean spiral that meets the minimum Fourier sampling criteria. A total of 1200 images were acquired during experiments using 100 uA current resulting in scan durations of 36 seconds. The phase of the RF pulse was cycled using a 180 degree step. In order to explore the sensitivity of the bSSFP signal to static off-resonance, a static linear gradient (0.5 Gauss/meter) along the x axis was applied, which resulted in a characteristic periodic banding artifact. The mean difference images were calculated by subtracting mean images of each steady state from the average of the steady state images and averaging 275 difference images (nreps=1100, initial 100 discarded to eliminate relaxation effects).

In an example, an electric current phantom was used as a model system for evaluating mABSS sensitivity to dynamic BMS and neural current contrast. This approach can provide a rapid method for initial evaluation of pulse sequence performance at high temporal resolution (e.g., 20-30 ms, or another resolution), since it does not require manipulation of SCAs. A spherical current phantom 100 mm in diameter filled with agar was used. The phantom recipe used $NiCl_2$ and an agar mixture such that T1 and T2 (100-110 ms) were comparable to grey matter; NaCl was added to increase the conductivity to mimic the RF load of a head. An insulated copper wire (~0.6 mm in diameter) was placed in the middle of the phantom along the x-y direction and perpendicular to the $B_0$ vector of the 3T scanner. Cables delivering current to the phantom were arranged parallel to the $B_0$ vector so that only the magnetic field created by current flowing in the perpendicular wire contributed to $B_0$. A ~9 k$\Omega$ resistor was connected in series to the phantom wire. The current magnitude was controlled with synchronization precision of 20 us via an analog output port of a National Instruments I/O card that received trigger TTL pulses from the scanner with every RF pulse. The card was programmed using LabView (National Instruments, Austin, Tex.) to set a desired temporal waveform locked to scanner RF pulses.

Example SNR analysis of the mABSS signal is presented. The example was analyzed in the absence of thermal and physiological noise. Spoiled MR pulse sequences sample phase-perturbing factors independently for each successive TR interval, since in any given TR interval the transverse magnetization and hence memory of the past perturbations is destroyed after acquisition. By contrast, bSSFP sequences do not spoil transverse magnetization and thus each of the multiple steady states of mABSS carries information about previous perturbations, which is reflected in their sensitivity to the order of perturbing signal values (see FIGS. 20A, 20B, 21A, 21B, 22A, 22B, 23A, 23B). The persistence of magnetization across multiple states may result in (i) robustness to (i.i.d.) noise and (ii) the whole of the perturbing waveform being encoded in all steady states. Therefore, while spoiled sequences may fail to produce significant signal for waveform bins containing weak signal, mABSS encodes all bins of the input waveform, including those perturbed weakly or not at all, in N steady state signals.

FIG. 3 plots an example of simulated mABSS SNR given a waveform of spin phase perturbations (N=4) of magnitude consistent with ncMRI (spin phase perturbations of $\delta\phi_j$=[0, 0.6,−0.3,0.1] degrees/TR, TR=20 ms). For this example, standard deviation for the injected phase noise (Gaussian i.i.d.) is equal to the mean of the absolute magnitude of input waveform bins (input $SNR_{IN}$=1). The evolution of the magnetization was calculated for 4100 rf excitations using Bloch equation simulation and the initial transient (100 rf) was discarded before calculating SNR (1000 waveform repeats were used).

Figure 24C:
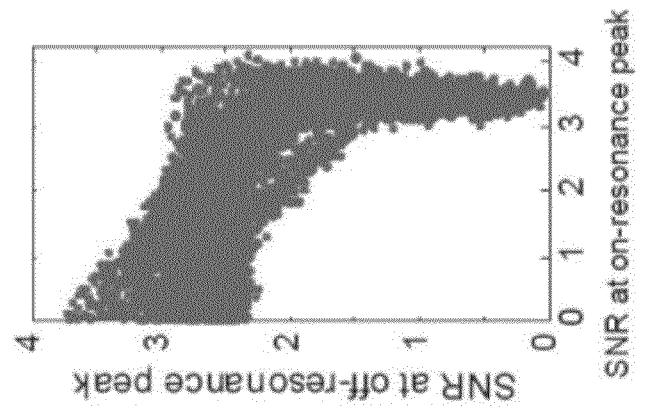
FIG. 24C is a plot illustrating properties of a signal to noise ratio of an example simulated magnetic resonance signal.
Figure 24B:
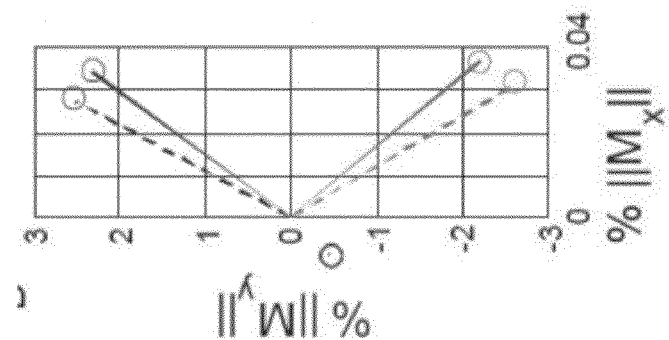
FIG. 24B is a plot illustrating complex amplitudes of example steady states.
Figure 24A:
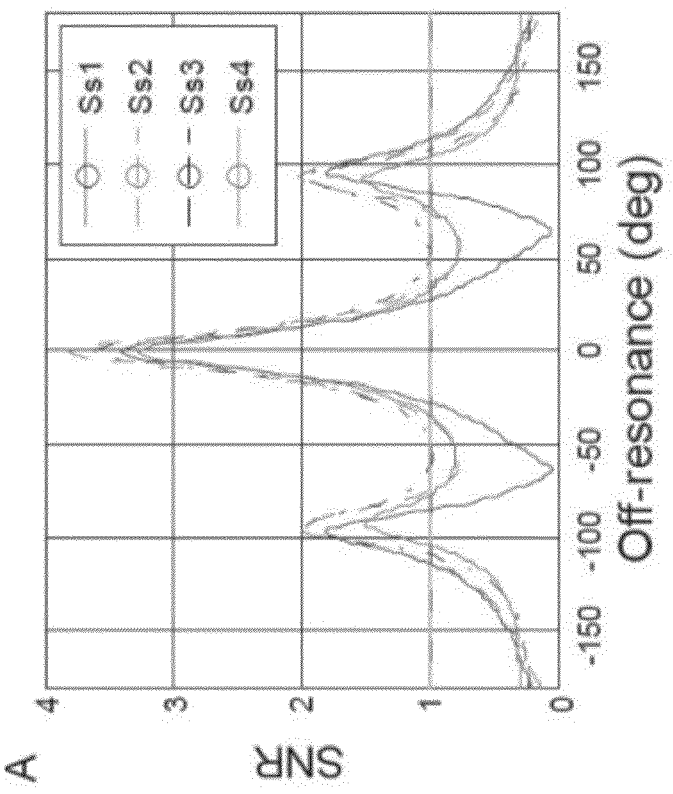
FIG. 24A is a plot illustrating a signal to noise ratio of an example simulated magnetic resonance signal.

Since spoiled sequences typically do not preserve transverse magnetization beyond one TR, in the ideal case of input noise only (no additional noise sources such as thermal and physiological noise), the signal $SNR_{OUT}$=$SNR_{IN}$=1, as shown by the grey broken line of FIG. 24A. By contrast, the SNR of the mABSS output can be improved for some intervals of the off-resonance profile. Due to the sensitivity of mABSS off-resonance profiles to the input waveform shape, however, the locations of the SNR peaks along off-resonance profile may vary. For example, for N=4 there is a peak at on-resonance and two symmetric peaks at approximately ±90 degrees. FIG. 24C plots SNR at the center vs. side peaks for 5000 randomly generated 4-bin waveforms (1000 waveform repeats were used). The (binned) waveform estimation can be further improved by using multiple acquisitions with different phase cycling steps in order to perform signal estimation at both the center and side peaks.

FIG. 24A shows a simulated off-resonance SNR profile (one period) of mABSS signal modulation when a noisy four bin waveform is applied resulting in spin phase rotations of $\delta\phi_j$=[0,0.6,−0.3,0.1] degrees/TR. The standard deviation of the additive noise equals the mean absolute waveform amplitude. Thus, input $SNR_{IN}$=1. The SNR profile is calculated for each of four resulting steady states: mean(abs($SS_i$−$SS_0$))/std, where std is the standard deviation of the difference abs($SS_i$−$SS_0$). FIG. 24B shows an MABSS encoded waveform shape in complex amplitudes of its steady states resolvable using quadrature detection. FIG. 24C shows center (on-resonance) vs. side-band peak SNR for simulated 5000 waveforms of the same mean perturbation amplitude (0.25 degrees/TR). In some implementations, SNR advantage of the bSSFP given the same perturbation magnitude effect at ceteris paribus is diminished as the duration of periodic waveform increases Tw approaching T2.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Only a few implementations and examples are described and other implementations, enhancements and variations can be made based on what is described and illustrated in this application.

What is claimed is:

1. A method of magnetic resonance imaging (MRI), comprising:
    magnetizing a sample comprising nuclear spins using a principle magnetic field generated external to the sample;
    applying to the sample a periodic pulse sequence comprising a plurality of radio frequency (rf) pulses and a plurality of recovery times between the rf pulses, wherein the pulse sequence is configured to generate, in the presence of a time-dependent magnetic field perturbation in the sample, a sequence of at least three different steady states of magnetization in the sample during each period of the pulse sequence; and
    processing a magnetic resonance signal acquired from the sample when under application of the periodic pulse sequence to identify characteristics of the magnetic field perturbation.

2. The method of claim 1, wherein processing a magnetic resonance signal acquired from the sample to identify characteristics of a magnetic field perturbation in the sample comprises processing a magnetic resonance signal acquired from the sample to identify a phase applied to the magnetization by the magnetic field perturbation during each period of the pulse sequence.

3. The method of claim 1, wherein the time duration of each period of the pulse sequence is based at least in part on a period of a magnetic field perturbation in the sample.

4. The method of claim 1, wherein processing a magnetic resonance signal acquired from the sample to identify characteristics of a magnetic field perturbation in the sample comprises processing a magnetic resonance signal acquired from the sample to identify characteristics of an electric current in the sample.

5. The method of claim 1, wherein the sample comprises at least part of a nervous system and processing a magnetic resonance signal acquired from the sample to identify characteristics of a magnetic field perturbation in the sample comprises processing a magnetic resonance signal acquired from the sample to identify characteristics of a neuronal current in the nervous system.

6. The method of claim 5, wherein the sample comprises at least part of a central nervous system.

7. The method of claim 5, wherein the sample comprises at least part of a peripheral nervous system.

8. The method of claim 1, wherein the sample comprises a blood vessel and processing a magnetic resonance signal acquired from the sample to identify characteristics of a magnetic field perturbation in the sample comprises processing a magnetic resonance signal acquired from the sample to identify characteristics of a fluid flow in the blood vessel.

9. The method of claim 1, wherein processing a magnetic resonance signal acquired from the sample to identify characteristics of a magnetic field perturbation in the sample comprises processing a magnetic resonance signal acquired from the sample to identify characteristics of mechanical perturbations applied to the sample.

10. The method of claim 1, wherein the characteristics comprise at least one of a location of the magnetic field perturbation, a spatial distribution of the magnetic field perturbation, an amplitude of the magnetic field perturbation, or a time-dependent waveform of the magnetic field perturbation.

11. The method of claim 1, further comprising applying a motion sensitizing gradient.

12. The method of claim 11, wherein applying a motion sensitizing gradient to the sample comprises controlling the motion sensitizing gradient to measure characteristics of diffusion in the sample.

13. The method of claim 1, further comprising inducing the magnetic field perturbation in sample.

14. The method of claim 13, wherein inducing the magnetic field perturbation in the sample comprises mechanically perturbing the sample.

15. The method of claim 13, wherein inducing the magnetic field perturbation in the sample comprises inducing the magnetic field perturbation in the sample in a periodic manner, and the time duration of each period of the pulse sequence is based at least in part on a period of the induced magnetic field perturbation.

16. The method of claim 13, wherein the sample comprises at least a portion of a living organism, and inducing the magnetic field perturbation comprises presenting a sensory stimulus to the living organism.

17. A method of magnetic resonance imaging (MRI), comprising:
  magnetizing a sample comprising nuclear spins using a principle magnetic field generated external to the sample;
  applying to the sample a periodic pulse sequence comprising a plurality of radio frequency (rf) pulses and a plurality of recovery times between the rf pulses, wherein the pulse sequence is configured to generate, in the presence of a time-dependent magnetic field perturbation in the sample, a sequence of at least two different steady states of magnetization in the sample during each period of the pulse sequence; and
  processing a magnetic resonance signal acquired from the sample when under application of the periodic pulse sequence to identify characteristics of an electric current in the sample.

18. The method of claim 17, wherein processing a magnetic resonance signal acquired from the sample to identify characteristics of an electric current in the sample comprises processing a magnetic resonance signal acquired from the sample to identify an amplitude of a magnetic field perturbation generated by the electric current.

19. The method of claim 17, wherein processing a magnetic resonance signal acquired from the sample to identify characteristics of an electric current in the sample comprises processing a magnetic resonance signal acquired from the sample to identify a time-dependent waveform of a magnetic field perturbation generated by the electric current.

20. The method of claim 17, wherein processing a magnetic resonance signal acquired from the sample to identify characteristics of an electric current in the sample comprises processing a magnetic resonance signal acquired from the sample to identify a spatial distribution of a magnetic field perturbation generated by the electric current.

21. The method of claim 17, wherein the sample comprises at least part of a nervous system and processing a magnetic resonance signal acquired from the sample to identify characteristics of an electric current in the sample comprises processing a magnetic resonance signal acquired from the sample to identify characteristics of a neuronal current in the nervous system.

22. A computer program product, embodied on a non-transitory computer-readable medium, operable to cause a data processing apparatus to perform operations comprising:
  generating signals for applying to a sample a periodic pulse sequence comprising a plurality of radio frequency (rf) pulses and a plurality of recovery times between the rf pulses, wherein the pulse sequence is configured to generate a sequence of at least three different steady states of magnetization in the sample during each period of the pulse sequence; and
  processing a magnetic resonance signal acquired from the sample when under application of the periodic pulse sequence to identify characteristics of a magnetic field perturbation in the sample.

23. The computer program product of claim 22, wherein the time duration of each period of the pulse sequence is based at least in part on a period of a magnetic field perturbation in the sample.

24. The computer program product of claim 22, wherein processing a magnetic resonance signal acquired from the sample to identify characteristics of a magnetic field perturbation in the sample comprises processing a magnetic resonance signal acquired from the sample to identify characteristics of an electric current in the sample.

25. The computer program product of claim 22, wherein the sample comprises at least part of a nervous system and processing a magnetic resonance signal acquired from the sample to identify characteristics of a magnetic field perturbation in the sample comprises processing a magnetic resonance signal acquired from the sample to identify characteristics of a neuronal current in the nervous system.

26. The computer program product of claim 22, wherein the characteristics comprise at least one of a location of the magnetic field perturbation, a spatial distribution of the magnetic field perturbation, an amplitude of the magnetic field perturbation, or a time-dependent waveform of the magnetic field perturbation.

27. A magnetic resonance imaging (MRI) system comprising:
  a radio frequency (rf) system configured to apply to a sample a periodic pulse sequence comprising a plurality of radio frequency (rf) pulses and a plurality of recovery times between the rf pulses and to detect a magnetic resonance signal from the sample in response to the periodic pulse sequence, wherein the pulse sequence is configured to generate, in the presence of a time-dependent magnetic field perturbation in the sample, a sequence of at least three different steady states of magnetization in the sample during each period of the pulse sequence; and
  a data processing apparatus configured to process the magnetic resonance signal acquired from the sample when under application of the periodic pulse sequence to identify characteristics of a magnetic field perturbation in the sample.

28. The MRI system of claim 27, wherein the time duration of each period of the pulse sequence is based at least in part on a period of a magnetic field perturbation in the sample.

29. The MRI system of claim 27, wherein processing a magnetic resonance signal acquired from the sample to identify characteristics of a magnetic field perturbation in the sample comprises processing a magnetic resonance signal acquired from the sample to identify characteristics of an electric current in the sample.

30. The MRI system of claim 27, wherein the sample comprises a nervous system and processing a magnetic resonance signal acquired from the sample to identify characteristics of a magnetic field perturbation in the sample comprises processing a magnetic resonance signal acquired from the sample to identify characteristics of a neuronal current in the nervous system.

31. The MRI system of claim 27, wherein the characteristics comprise at least one of a location of the magnetic field perturbation, a spatial distribution of the magnetic field perturbation, an amplitude of the magnetic field perturbation, or a time-dependent waveform of the magnetic field perturbation.

32. A method comprising:
  applying a periodic pulse sequence to a nervous system, the pulse sequence comprising a plurality of radio frequency (rf) pulses and a plurality of recovery times between the rf pulses, wherein the pulse sequence is configured to generate, in the presence of a time-dependent magnetic field perturbation in the nervous system, multiple different steady states of magnetization in the nervous system during each period of the pulse sequence; and processing a magnetic resonance signal acquired from the nervous system when under application of the periodic pulse sequence to obtain characteristics of neuronal activity associated with the magnetic field perturbation.

33. The method of claim 32, wherein the neuronal activity comprises an electric current that generates the magnetic field perturbation.

34. The method of claim 33, wherein the period of the pulse sequence is synchronized with a period of the magnetic field perturbation.

35. The method of claim 32, wherein the magnetic field perturbation has a period less than or equal to one hundred (100) milliseconds.

36. The method of claim 35, wherein the magnetic field perturbation has a period greater than or equal to ten (10) milliseconds.

37. The method of claim 32, wherein the sample comprises a contrast agent that tracks correlates of neuronal activity.

38. The method of claim 37, wherein the contrast agent comprises a smart contrast agent having at least one of a T2 relaxation rate or a bulk susceptibility that changes as a function of $Ca^{++}$ concentration in the nervous system.

* * * * *